United States Patent
Moon

(10) Patent No.: US 12,336,801 B2
(45) Date of Patent: Jun. 24, 2025

(54) INDICATOR DETERMINATION

(71) Applicant: Impedimed Limited, Pinkenba (AU)

(72) Inventor: Jordan Robert Moon, Lexington, KY (US)

(73) Assignee: Impedimed Limited, Pinkenba (AU)

( * ) Notice: Subject to any disclaimer, the term of this patent is extended or adjusted under 35 U.S.C. 154(b) by 56 days.

(21) Appl. No.: 16/622,564

(22) PCT Filed: Jun. 8, 2018

(86) PCT No.: PCT/AU2018/050574
§ 371 (c)(1),
(2) Date: Dec. 13, 2019

(87) PCT Pub. No.: WO2018/227238
PCT Pub. Date: Dec. 20, 2018

(65) Prior Publication Data
US 2021/0145303 A1    May 20, 2021

Related U.S. Application Data

(60) Provisional application No. 62/519,697, filed on Jun. 14, 2017.

(51) Int. Cl.
*A61B 5/0537* (2021.01)
*A61B 5/00* (2006.01)
(Continued)

(52) U.S. Cl.
CPC ........ *A61B 5/0537* (2013.01); *A61B 5/02055* (2013.01); *A61B 5/4875* (2013.01);
(Continued)

(58) Field of Classification Search
CPC .... A61B 5/0537; A61B 5/4875; A61B 5/4881
See application file for complete search history.

(56) References Cited

U.S. PATENT DOCUMENTS

2006/0041280 A1    2/2006  Stahmann et al.
2009/0043222 A1    2/2009  Chetham
(Continued)

FOREIGN PATENT DOCUMENTS

WO    WO 2016/196080    12/2016

OTHER PUBLICATIONS

International Search Report and Written Opinion dated Sep. 17, 2018 for Application No. PCT/AU2018/050574.

*Primary Examiner* — Lynsey C Eiseman
*Assistant Examiner* — Jessica L Mullins
(74) *Attorney, Agent, or Firm* — Knobbe, Martens, Olson & Bear, LLP

(57) ABSTRACT

A system for generating an indicator at least in part relating to fluid levels in a biological subject, the system including one or more processing devices that, in response to at least one impedance measurement performed on the subject determine a parameter value at least in part using results of the at least one impedance measurement, perform an assessment to determine if the parameter value is indicative of a meaningful change in a subject normal, the subject normal being based on results of a plurality of previous impedance measurements and use results of the assessment to generate an indicator indicative of fluid levels or selectively update the subject normal.

15 Claims, 16 Drawing Sheets

(51) Int. Cl.
    *A61B 5/0205*    (2006.01)
    *G16H 40/67*     (2018.01)
    *G16H 50/20*     (2018.01)
    *G16H 50/30*     (2018.01)
    *A61B 5/01*      (2006.01)
    *A61B 5/021*     (2006.01)
    *A61B 5/024*     (2006.01)
    *A61B 5/0295*    (2006.01)
    *A61B 5/08*      (2006.01)
    *A61B 5/145*     (2006.01)
    *A63B 24/00*     (2006.01)
    *G16H 20/30*     (2018.01)

(52) U.S. Cl.
    CPC .......... *A61B 5/7267* (2013.01); *A61B 5/7275* (2013.01); *A61B 5/742* (2013.01); *G16H 40/67* (2018.01); *G16H 50/20* (2018.01); *G16H 50/30* (2018.01); *A61B 5/01* (2013.01); *A61B 5/021* (2013.01); *A61B 5/024* (2013.01); *A61B 5/0295* (2013.01); *A61B 5/0806* (2013.01); *A61B 5/0816* (2013.01); *A61B 5/14542* (2013.01); *A61B 5/14546* (2013.01); *A61B 5/4866* (2013.01); *A61B 5/4878* (2013.01); *A63B 24/0062* (2013.01); *G16H 20/30* (2018.01)

(56) References Cited

U.S. PATENT DOCUMENTS

2009/0275854 A1   11/2009  Zielinski et al.
2016/0354032 A1*  12/2016  Wariar ................ A61B 5/4875

* cited by examiner

INDICATOR DETERMINATION

RELATED APPLICATIONS

This application is a U.S. National Phase under 35 U.S.C. 371 of the International Patent Application No. PCT/AU2018/050574, filed Jun. 8, 2018, and published in English on Dec. 20, 2018 as WO 2018/227238, which claims the benefit of U.S. Provisional Application No. 62/519,697, filed Jun. 14, 2017, all of which are incorporated by reference in their entirety.

BACKGROUND OF THE INVENTION

The present invention relates to a method and system for use in determining an indicator relating to measurements performed on a biological subject and in one particular example to an indicator at least in part relating to fluid levels in a biological subject determined using impedance measurements.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

It is known to perform impedance measurements for a variety of reasons, for example to determine body composition indicators, as well as indicators of medical conditions, such as heart failure or oedema indicators. Such impedance measurements are typically subject to a combination of short and long term variations. For example, measurements will vary throughout a day based on a subject's relative hydration levels, which in turn depend on factors such as fluid intake, alcohol or caffeine consumption, exercise, or the like. Additional short term variations can arise due to inaccuracies in measurement processes, such as variations in surface contact between electrodes and the subject. In addition to this, longer term variations arise, for example due to changes in long term physical conditions, such as changes in severity of a medical condition.

Existing devices typically operate by simply displaying an indication of a current measured value, or derived indicator value, meaning it is difficult for a user to distinguish between short term and long term variations. Consequently, it is difficult to ascertain whether changes in measured values are meaningful long term variations, or spurious outcomes of the measurement process.

Similar issues also arise with other measurements. For example, weight measurements can fluctuate on a day to day basis due to fluid retention, inaccuracies in the measurement equipment and a range of other factors, but these changes do not necessarily represent a meaningful long term change in weight.

SUMMARY OF THE PRESENT INVENTION

In one broad form an aspect of the present invention seeks to provide a system for generating an indicator at least in part relating to fluid levels in a biological subject, the system including one or more processing devices that, in response to at least one impedance measurement performed on the subject: determine a parameter value at least in part using results of the at least one impedance measurement; perform an assessment to determine if the parameter value is indicative of a meaningful change in a subject normal, the subject normal being based on results of a plurality of previous impedance measurements; use results of the assessment to at least one of: generate an indicator indicative of fluid levels; and, selectively update the subject normal.

In one embodiment the subject normal is at least one of: a subject normal value; and, a subject normal range.

In one embodiment the one or more processing devices perform the assessment at least in part using machine learning techniques.

In one embodiment the one or more processing devices perform the assessment using a computational model embodying a relationship between the parameter value and the subject normal, the computational model being obtained by applying machine learning to reference parameter values and subject normal measured for one or more reference subjects.

In one embodiment the one or more processing devices: determine at least one metric; and, apply the at least one metric to the computational model.

In one embodiment the at least one metric is indicative of at least one of: the parameter value including at least one of: an impedance value indicative of a measured impedance; an impedance parameter value derived from at least one impedance value; and, a body state value derived from at least one of: at least one impedance value; and, at least one impedance parameter value. a vital sign indicator indicative of at least one of: a cardiac parameter value; a respiratory parameter value; a blood potassium level; a temperature; a tissue temperature; a blood pressure; a respiratory rate; a heart rate; and, a blood oxygenation level; and, a measurement attribute including at least one of: an exercise indicator indicative of participation in exercise; a time of day; a clothing state; a consumption of feed or beverage; a weight; details of one or more medical symptoms.

In one embodiment the at least one metric is indicative of at least one of: whether the parameter value falls outside a subject normal range, the subject normal range being at least partially based on results of a plurality of previous impedance measurements; a number of parameter values falling outside a subject normal range in a defined time period; changes in parameter values; a trend in parameter values; and, a magnitude of changes in parameter values.

In one embodiment the one or more processing devices perform the assessment by: comparing the parameter value to a subject normal range, the subject normal range being at least partially based on results of a plurality of previous impedance measurements; and, determining if the parameter value is indicative of a meaningful change in accordance with results of the comparison.

In one embodiment the one or more processing devices perform the assessment by: determining if the parameter value falls outside a subject normal range, the subject normal range being at least partially based on results of a plurality of previous impedance measurements; updating a count indicative of a number of parameter values that fall outside the subject normal range in accordance with results of the determination; determining if the count exceeds a threshold; and, based on whether the count exceeds the threshold: determining if the parameter value is indicative of a meaningful change in a subject normal; generating the indicator; and, selectively updating the subject normal range.

In one embodiment the count is indicative of at least one of: a number of sequential parameter values that fall outside the subject normal range and wherein the one or more processing devices reset the count if the parameter value falls inside the subject normal range; and, how many of a defined number of impedance measurements fall outside the subject normal range.

In one embodiment the indicator is indicative of at least one of: the parameter value; a subject normal value; a subject normal range; a subject normal parameter value derived from a subject normal value; whether the parameter value is greater than or lesser than a subject normal value; whether the parameter value is greater than or lesser than a subject normal parameter value; whether the parameter value falls outside the subject normal range; whether the parameter value is greater than or lesser than the subject normal range; a magnitude of a difference between the parameter value and a subject normal value; a magnitude of a difference between the parameter value and a subject normal parameter value; a parameter value change; a parameter value rate of change; and, a parameter value trend.

In one embodiment: if the parameter value is not indicative of a meaningful change in a subject normal, the indicator is indicative of at least one of: a subject normal value; that there is no meaningful change from the subject normal value; and, a trend indicative of a direction of change of the parameter value relative to the subject normal value; and if the parameter value is indicative of a meaningful change in a subject normal, the indicator is indicative of at least one of: the parameter value; and, an updated subject normal value.

In one embodiment the parameter value is at least one of: an impedance value indicative of a measured impedance; an impedance parameter value derived from at least one impedance value; and, a body state value derived from at least one of: at least one impedance value; and, at least one impedance parameter value.

In one embodiment the subject normal range is based on a subject normal value.

In one embodiment the subject normal range includes at least one of: a subject normal impedance value range; a subject normal parameter value range; and, a subject normal body state value range.

In one embodiment the one or more processing devices calculate the parameter value by: retrieving a subject normal parameter value and a subject normal impedance value; determining a measured impedance value; determining a difference between the subject normal impedance value and the measured impedance value; and, calculate the parameter value using the subject normal parameter value and the change in impedance.

In one embodiment the one or more processing devices calculate the parameter value using the equation: $PV = B_{PV} + x\Delta I$ where: PV is the parameter value $B_{PV}$ is the subject normal parameter value x is a coefficient $\Delta I$ is the difference between the subject normal impedance value and the measured impedance value.

In one embodiment the one or more processing devices: determine a plurality of parameter values, the plurality of parameter values being selected ones of multiple parameter values derived from multiple impedance measurements; and, calculate, using the plurality of parameter values, at least one of: a subject normal value; a subject normal range; and, a body state value.

In one embodiment the one or more processing devices calculate a subject normal value using at least one of: an average of a plurality of impedance parameter values. an average of a plurality of parameter values; and, an average of a plurality of body state values.

In one embodiment the one or more processing devices calculate the subject normal range using at least one of: a spread of at least one of: a plurality of impedance measurements; a plurality of parameter values; and, a plurality of body state values; and, a predetermined range from a subject normal value.

In one embodiment the one or more processing devices calculate the subject normal range taking into account at least one of: details of one or more medical symptoms; one or more vital signs parameter values; and, one or more subject attributes.

In one embodiment the one or more processing devices: assess if the parameter value falls outside a first subject normal range; selectively update a first count indicative of a number of parameter values falling outside of the first subject normal range; determine if the first count exceeds a first threshold; and, displays the indicator based on a result of the determination.

In one embodiment the one or more processing devices: assess if the parameter value falls outside a second subject normal range; selectively update a second count indicative of a number of parameter values falling outside of the second subject normal range; determine if the second count exceeds a second threshold; and, selectively performs an action based on a result of the determination.

In one embodiment the action includes at least one of: updating the subject normal range; updating the subject normal value; and, generating a notification.

In one embodiment the one or more processing devices determine a threshold taking into account at least one of: details of one or more medical symptoms; one or more vital signs parameter values; and, one or more subject attributes.

In one embodiment the one or more processing devices selectively calculate a new subject normal value in response user input commands.

In one embodiment the one or more processing devices calculate, using impedance measurements meeting defined measurement criteria, at least one of: a parameter value; a subject normal value; and, a subject normal range.

In one embodiment the one or more processing devices: determine measurement attributes; and compare the measurement attributes to defined measurement criteria to determine if an impedance measurement should be used in calculating at least one of: a parameter value; a subject normal value; and, a subject normal range.

In one embodiment the one or more processing devices: determine measurement attributes; compare the measurement attributes to defined measurement criteria; determining a compensation factor in accordance with results of the comparison; and, using the compensation factor to selectively modify at least one of: an impedance value indicative of a measured impedance; an impedance parameter value derived from at least one impedance value; and, a body state value derived from at least one of: at least one impedance value; and, at least one impedance parameter value.

In one embodiment the one or more processing devices: determine a subject identifier indicative of an identity of the subject; and, determine the defined measurement criteria using the subject identifier.

In one embodiment the defined measurement criteria are retrieved from stored user data associated with the subject.

In one embodiment the measurement attributes include at least one of: an exercise indicator indicative of participation in exercise; a time of day; a clothing state; a consumption of feed or beverage; a weight; a vital sign indicator; and, details of one or more medical symptoms.

In one embodiment the one or more processing devices: determine at least one parameter value change using multiple parameter values; and, selectively use the parameter value change to determine a parameter value trend indicative of at least one of: a direction of parameter value change; a rate of parameter value change; and, a magnitude of parameter value change.

In one embodiment the one or more processing devices: compare the parameter value change to a change threshold; and, selectively determine the parameter value trend based on results of the comparison.

In one embodiment the multiple parameter values include at least one of: sequential parameter values; a current parameter value and a normal parameter value; and, a current parameter value and an nth previous parameter value.

In one embodiment the one or more processing devices use the parameter value trend to predict at least one of: a future parameter value; a future subject normal value; a future subject normal range; and, a time needed to reach a target.

In one embodiment the one or more processing devices use the parameter value trend to generate an indicator.

In one embodiment the system includes a measuring system that performs impedance measurements and provides an indication of at least one measured impedance to the one or more processing devices via a communications network.

In one embodiment the measuring system includes: a measuring device; and, a client device in communication with the measuring device, wherein the client device: receives measurement data indicative of at least one impedance measurement performed on the subject; and, provides subject data to the one or more processing devices via a communications network, the subject data being indicative of at least one of: a user identifier associated with the user; the measurement data; one or more measured impedance values; one or more parameter values; one or more vital signs indicators; and, one or more measurement attributes.

In one embodiment the measuring device includes: at least one signal generator electrically connected to drive electrodes to apply a drive signal to a user; at least one sensor electrically connected to sense electrodes to measure a response signal in the user; a measuring device processor that at least in part: controls the at least one signal generator; receives an indication of a measured response signal from the at least one sensor; and, generates measurement data indicative of at least one measured impedance value.

In one embodiment the vital signs indicators include at least one of: a cardiac parameter value; a respiratory parameter value; a blood potassium level; a temperature; a tissue temperature; a blood pressure; a respiratory rate; a heart rate; and, a blood oxygenation level.

In one broad form an aspect of the present invention seeks to provide a system for generating an indicator in response to measurements performed on a biological subject, the system including one or more processing devices that: determine a parameter value at least in part using results of at least one measurement; determine if the parameter value falls outside a subject normal range, the subject normal range being at least partially based on results of a plurality of previous measurements; update a count indicative of a number of parameter values that fall outside the subject normal range in accordance with results of the determination; determine if the count exceeds a threshold; and, based on whether the count exceeds the threshold: generate the indicator; and, selectively update the subject normal range.

In one broad form an aspect of the present invention seeks to provide a method for determining an indicator at least in part relating to fluid levels in a biological subject, the method including in one or more processing devices, in response to at least one impedance measurement performed on the subject: determining a parameter value at least in part using results of the at least one impedance measurement; determining if the parameter value falls outside a subject normal range, the subject normal range being at least partially based on results of a plurality of previous impedance measurements; updating a count indicative of a number of parameter values that fall outside the subject normal range in accordance with results of the determination; determining if the count exceeds a threshold; and, based on whether the count exceeds the threshold: generating the indicator; and, selectively updating the subject normal range.

In one broad form an aspect of the present invention seeks to provide a method for generating an indicator in response to measurements performed on a biological subject, the method including in one or more processing devices: determining a parameter value at least in part using results of at least one measurement; determining if the parameter value falls outside a subject normal range, the subject normal range being at least partially based on results of a plurality of previous measurements; updating a count indicative of a number of parameter values that fall outside the subject normal range in accordance with results of the determination; determining if the count exceeds a threshold; and, based on whether the count exceeds the threshold: generating the indicator; and, selectively updating the subject normal range.

In one broad form an aspect of the present invention seeks to provide a system for determining an indicator at least in part relating to fluid levels in a biological subject, the system including one or more processing devices that, in response to at least one impedance measurement performed on the subject: determine a parameter value at least in part using results of the at least one impedance measurement; determine measurement attributes associated with at least one impedance measurement; compare the measurement attributes to defined measurement criteria; if the measurement criteria meet the defined criteria: determine if the parameter value falls outside a subject normal range, the subject normal range being at least partially based on results of a plurality of previous impedance measurements; based on the result of the determination: display an indicator; and, selectively update the subject normal range; and, if the measurement criteria do not meet the defined criteria, at least one of: display an indicator based on the parameter value; and, determine a compensation factor in accordance with results of the comparison, the compensation factor being used to selectively modify at least one of: an impedance value indicative of a measured impedance; an impedance parameter value derived from at least one impedance value; and, a body state value derived from at least one of: at least one impedance value; and, at least one impedance parameter value.

In one embodiment the one or more processing devices: determine a subject identifier indicative of an identity of the subject; and, determine the defined measurement criteria using the subject identifier.

In one embodiment the defined measurement criteria are retrieved from stored user data associated with the subject.

In one embodiment the measurement attributes include at least one of: an exercise indicator indicative of participation in exercise; a time of day; a clothing state; a consumption of feed or beverage; a weight; a vital sign indicator; and, details of one or more medical symptoms.

In one broad form an aspect of the present invention seeks to provide a system for generating an indicator in response to measurements performed on a biological subject, the system including one or more processing devices that: determine a parameter value at least in part using results of at least one measurement; perform an assessment to determine if the parameter value is indicative of a meaningful change in a subject normal, the subject normal being at least partially based on results of a plurality of previous measurements; use results of the assessment to at least one of: generate the indicator; and, selectively update the subject normal.

In one broad form an aspect of the present invention seeks to provide a method for generating an indicator at least in part relating to fluid levels in a biological subject, the method including in one or more processing devices, in response to at least one impedance measurement performed on the subject: determining a parameter value at least in part using results of the at least one impedance measurement; performing an assessment to determine if the parameter value is indicative of a meaningful change in a subject normal, the subject normal being based on results of a plurality of previous impedance measurements; using results of the assessment to at least one of: generate an indicator indicative of fluid levels; and, selectively update the subject normal.

In one broad form an aspect of the present invention seeks to provide a method for generating an indicator in response to measurements performed on a biological subject, the method including in one or more processing devices: determining a parameter value at least in part using results of at least one measurement; performing an assessment to determine if the parameter value is indicative of a meaningful change in a subject normal, the subject normal being at least partially based on results of a plurality of previous measurements; using results of the assessment to at least one of: generate the indicator; and, selectively update the subject normal.

In one broad form an aspect of the present invention seeks to provide a system for determining an indicator at least in part relating to fluid levels in a biological subject, the system including one or more processing devices that, in response to at least one impedance measurement performed on the subject: determine a parameter value at least in part using results of the at least one impedance measurement; determine if the parameter value falls outside a subject normal range, the subject normal range being at least partially based on results of a plurality of previous impedance measurements; update a count indicative of a number of parameter values that fall outside the subject normal range in accordance with results of the determination; determine if the count exceeds a threshold; and, based on whether the count exceeds the threshold: generate the indicator; and, selectively update the subject normal range.

In one broad form an aspect of the present invention seeks to provide a system for generating an indicator in response to measurements performed on a biological subject, the system including one or more processing devices that: determine a parameter value at least in part using results of at least one measurement; determine measurement attributes associated with at least one measurement; compare the measurement attributes to defined measurement criteria; if the measurement criteria meet the defined criteria: determine if the parameter value falls outside a subject normal range, the subject normal range being at least partially based on results of a plurality of previous measurements; based on the result of the determination: display an indicator; and, selectively update the subject normal range; and, if the measurement criteria do not meet the defined criteria, at least one of: display an indicator based on the parameter value; and, determine a compensation factor in accordance with results of the comparison, the compensation factor being used to selectively modify the parameter value.

In one broad form an aspect of the present invention seeks to provide a method for determining an indicator at least in part relating to fluid levels in a biological subject, the method including, in one or more processing devices, in response to at least one impedance measurement performed on the subject: determining a parameter value at least in part using results of the at least one impedance measurement; determining measurement attributes associated with at least one impedance measurement; comparing the measurement attributes to defined measurement criteria; if the measurement criteria meet the defined criteria: determining if the parameter value falls outside a subject normal range, the subject normal range being at least partially based on results of a plurality of previous impedance measurements; based on the result of the determination: displaying an indicator; and, selectively updating the subject normal range; and, if the measurement criteria do not meet the defined criteria, at least one of: displaying an indicator based on the parameter value; and, determining a compensation factor in accordance with results of the comparison, the compensation factor being used to selectively modify at least one of: an impedance value indicative of a measured impedance; an impedance parameter value derived from at least one impedance value; and, a body state value derived from at least one of: at least one impedance value; and, at least one impedance parameter value.

In one broad form an aspect of the present invention seeks to provide a method for generating an indicator in response to measurements performed on a biological subject, the method including In one or more processing devices: determining a parameter value at least in part using results of at least one measurement; determining measurement attributes associated with at least one measurement; comparing the measurement attributes to defined measurement criteria; if the measurement criteria meet the defined criteria: determining if the parameter value falls outside a subject normal range, the subject normal range being at least partially based on results of a plurality of previous measurements; based on the result of the determination: displaying an indicator; and, selectively updating the subject normal range; and, if the measurement criteria do not meet the defined criteria, at least one of: displaying an indicator based on the parameter value; and, determining a compensation factor in accordance with results of the comparison, the compensation factor being used to selectively modify the parameter value.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

Examples of various embodiments of the present invention will now be described with reference to the accompanying drawings, in which:—

DETAILED DESCRIPTION OF THE PREFERRED EMBODIMENTS

Figure 1A:
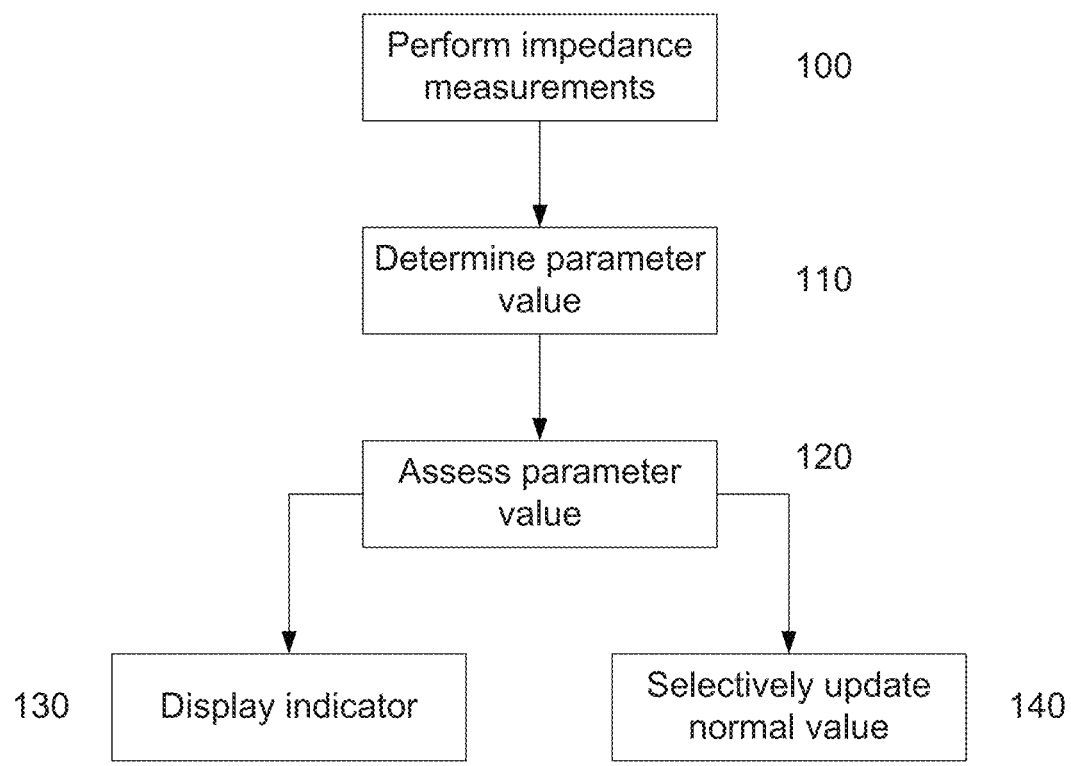
FIG. 1A is a flow chart of an example of a process for determining an indicator based on measurements of a biological subject.

An example of a method for determining an indicator based on measurements performed on a biological subject will now be described with reference to FIG. 1.

For the purpose of this example, the intention is to determine an indicator indicative of longer term variations arising in a biological subject, which therefore attempt to ignore short term variations, as may occur for example over the course of a day, or even on a day-to-day basis. For the purpose of illustration reference will be made to the use of impedance measurements, with the measurements being used to display an indicator that is based on a body state value, such as a fluid status, fluid levels, a body composition value, a disease state indicator indicative of a presence, absence, or degree of a medical condition such as heart failure, lymphedema, or the like. However, it will be appreciated that similar techniques could be applied to other measurements, such as measurements of weight, cardiac parameters, respiratory parameters, blood potassium levels, temperature, a blood pressure, heart rate, blood oxygenation levels or the like, and that reference to impedance measurements while exemplary, should not be construed as limiting.

For the purpose of illustration, it is also assumed that the process is performed at least in part using one or more electronic processing devices forming part of one or more processing systems, connected to one or more measuring systems, such as impedance measuring systems or the like. In one example, this is performed at least using a cloud based architecture that interfaces with measuring systems or other client devices, as will be described in more detail below.

For ease of explanation, the term "subject" refers to any animal that is being assessed, and more particularly a human, although this is not intended to be limiting and the techniques could be applied more broadly to other vertebrates and mammals. The terms "subject normal value" and "subject normal range" are intended to refer to a value and a range of values respectively, which are measured or derived for a subject, and which are typical for that subject. The subject normal range is determined taking into account a combination of factors including methodological, biological, and physiological factors, which can be dynamic and represent typical variation for that individual.

In this example, at step 100 impedance measurements are performed. The impedance measurements can be of any appropriate form and could include whole of body or segmental impedance measurements, and examples will be described in more detail below. The impedance measurements could be performed as part of the analysis process, or alternatively could be performed by a separate measuring device, with analysis being subsequently performed by the one or more processing devices, for example by retrieving results from a database, receiving the results from a measuring device or the like.

At step 110, a parameter value is determined at least in part using results of the impedance measurement. The parameter value can be of any appropriate form and could include an impedance value, such as a measured resistance, reactance or phase angle, an impedance parameter value derived from one or more measured impedance value(s), such as a value of impedance at zero or infinite frequency, or could include a body state value, such as a fluid status or body composition value, and further examples will be described in more detail below. The parameter value could be received directly from a measurement device, or retrieved from a data store, but more typically is calculated or derived from an impedance value using one or more appropriate calculations, as will be described in more detail below.

At step 120 an assessment is performed to determine if the parameter value is indicative of a meaningful change in a subject normal. The subject normal is typically based on a plurality of previous measurements performed on the subject, and may be established taking into account variations in the results of the previous impedance measurements. In one example, the subject normal is a range is based on an average and standard deviation of multiple parameter values derived from corresponding impedance measurements, although other suitable techniques for determining a subject normal range could be used. Similarly, a subject normal value could be based on an average of multiple parameter values.

The subject normal can be obtained in any appropriate manner, and could be calculated as required, but more typically is retrieved from a suitable data repository such as a database or the like, and optionally from user data associated with the respective subject. In this regard, the subject normal could be stored in the form of a range of subject impedance values, subject parameter values or subject body state values, depending on the preferred implementation. Thus, the subject normal range could be of a similar form to the parameter value, so that for example, if the parameter value is a value of a particular body composition parameter, the subject normal range could be stored as a normal range of values of the same body composition parameter. However, this is not essential, and alternatively the subject normal range could be stored as a normal range of subject impedance values, which is then used to calculate a normal range of body composition parameter values as required.

Whether the parameter value is indicative of a meaningful change can be assessed in any one of several ways. For example, this could include using machine learning, with this optionally involving using machine learning to derive a computational model which can be used in performing the assessment.

Once an assessment has been performed, results of the assessment can be used to display an indicator at step 130 and optionally determine of an updated subject normal at step 140. In this regard, the manner in which the indicator is displayed, or the form the indicator takes, will depend on whether or not the parameter value is indicative of a meaningful change. For example, if the change is meaningful, indicator could be displayed based on the current parameter value, whereas if the change is not meaningful, the indicator could be displayed based on the subject normal. Similarly the subject normal could be recalculated based on parameter values that represent a meaningful change, or could remain unchanged if the change is not meaningful.

Accordingly, the above described process provides a mechanism in order to evaluate parameter values derived from impedance measurements, in particular to determine if changes in the parameter values represent a meaningful change. In order to achieve this, the parameter values are assessed based on a subject normal that is at least in part based on previous measurements for the subject. For example, if a sufficient number of parameter values fall outside a subject normal range, this can be used to determine that changes are meaningful, allowing this to be communicated to a user through displaying of a suitable indicator and to allow a subject normal range to be recalculated. Alternatively, if it is determined that changes in the parameters values are not meaningful, then an indicator could be displayed based on the subject normal range.

It would be appreciated that displaying an indicator in this fashion ensures that the indicator is not subject to short term variations, such as day-to-day or within day variations, but rather is based on longer term variations established over a sufficiently large of number of measurements. Additionally, once a change in parameter values has been established as meaningful, this can be used to update the value of the subject normal range, thereby providing a dynamic subject normal range, allowing future measurements to be compared to the updated dynamic subject normal range.

In another example, impedance measurements can be compared to defined criteria, with results of the comparison being used to assess whether the impedance measurements can be used in displaying an indicator and/or calculating a subject normal range. In this example, if the criteria are met, calculated parameter values can be compared to a subject normal range, with results of the comparison being used to determine an indicator and/or calculate a new subject normal range. Alternatively, if the criteria are not met, the parameter value can simply be displayed. This can be used to ensure measurements are directly comparable and hence avoiding measurements impacted by external factors from unduly affecting the subject normal range or being otherwise considered as meaningful.

For example, fluid levels within a subject will change based on factors such as volumes of liquids consumed. Accordingly, by ensuring measurements are performed in a consistent manner, such as by ensuring measurements are completed prior to ingesting food or fluid, or exercising, ensures such external factors have minimal influence on displayed indicators and calculated subject normal ranges.

A number of further features will now be described.

As mentioned above, the assessment of whether a parameter value represents a meaningful change could be performed at least in part using machine learning techniques. In one example, this involves using a computational model embodying a relationship between the parameter value and the subject normal, the computational model being obtained by applying machine learning to reference parameter values and subject normal measured for one or more reference subjects.

In particular, this approach typically uses parameter values and subject normals from reference subjects to a generic machine learning model. The nature of the model and the training performed can be of any appropriate form and could include any one or more of decision tree learning, random forest, logistic regression, association rule learning, artificial neural networks, deep learning, inductive logic programming, support vector machines, clustering, Bayesian networks, reinforcement learning, representation learning, similarity and metric learning, genetic algorithms, rule-based machine learning, learning classifier systems, or the like. As such schemes are known, these will not be described in any further detail.

In this instance, the model is typically used by determining at least one metric and then applying the at least one metric to the computational model. The metrics can be of any appropriate form but are typically at least partially based on the parameter value. In this regard, the parameter value can be an impedance value indicative of a measured impedance, an impedance parameter value derived from at least one impedance value, or a body state value, such as a fluid level or body composition value derived from impedance value(s) and/impedance parameter value(s). Whilst the metric could be based solely on the parameter value, more typically the metric takes into account whether the parameter value falls outside a subject normal range, whether a number of parameter values fall outside a subject normal range in a defined time period, changes in parameter values, a trend in parameter values and a magnitude of changes in parameter values. Thus, this typically is based on not just a current measurement, but a number of measurements over time, to take into account whether the parameter value is a one-off value indicative of a short-term variation, or indicative of a more long term change.

In addition, metrics can be based on a vital sign indicator indicative of one or more of a cardiac parameter value, a respiratory parameter value, a blood potassium level, a temperature, a tissue temperature, a blood pressure, a respiratory rate, a heart rate, a blood oxygenation level, or the like. This can help assist in taking into account whether changes in fluid levels are indicative of a general trend or are more meaningful. For example, a meaningful change for a fit healthy individual might require a greater change than for a subject suffering from a medical condition, such as heart failure. In this latter case, even minor variations could be indicative of a significant worsening of the condition, and hence would need to be assessed as meaningful, so that the subject or another user is notified of resulting changes.

In another example, the metric can be based on a measurement attribute such as an exercise indicator indicative of participation in exercise, a time of day, a clothing state, a consumption of feed or beverage, a weight, details of one or more medical symptoms, or the like. This can be used to ensure measurements are directly comparable and hence avoiding measurements impacted by external factors from unduly affecting the subject normal range or being otherwise considered as meaningful.

Thus, the above described approach uses one or more computational models in order to assess whether a parameter value is indicative of a meaningful change in a subject normal, such as a normal range or normal value.

To achieve this the model is typically created by training the model with reference data collected from one or more reference subjects. In this example, reference subject data is obtained, which is at least partially indicative of parameter values and a subject normal, obtained from impedance measurements performed on the reference subject. The subject will also typically undergo an assessment to determine if the parameter value is indicative of a meaningful change in subject normal, which could be achieved by clinical assessment or by reviewing historical measurements. For example, this could be performed using non-machine learning techniques, such as the threshold assessment outlined below.

The reference subject data is analysed to determine at least one metric, which is then used to train the computational model. To achieve this, it is typical to use all potentially available metrics, including all parameters, changes in parameters, vital signs, measurement criteria and the like. This can be used in order to ascertain which of the metrics are most useful in identifying meaningful changes.

Following this, a combination of the reference metrics and one or more generic computational models are selected, with the reference metrics and assessment of the whether or not the parameter value represented a meaningful change being used to train the model(s). The nature of the model and the training performed can be of any appropriate form and could include any one or more of decision tree learning, random forest, logistic regression, association rule learning, artificial neural networks, deep learning, inductive logic programming, support vector machines, clustering, Bayesian networks, reinforcement learning, representation learning, similarity and metric learning, genetic algorithms, rule-based machine learning, learning classifier systems, or the like. As such schemes are known, these will not be described in any further detail.

In addition to simply generating the model, the process typically includes testing the model to assess the discriminatory performance of the trained model. Such testing is typically performed using a subset of the reference subject data, and in particular, different reference subject data to that used to train the model, to avoid model bias. The testing is used to ensure the computational model provides sufficient discriminatory performance.

As an alternative to using a computational model however, a threshold comparison approach can be used, and an example of this will now be described with reference to FIG. 1B. In this example, steps 100, 110, 130 and 14 are as described above and will not therefore be described in any further detail.

Figure 1B:
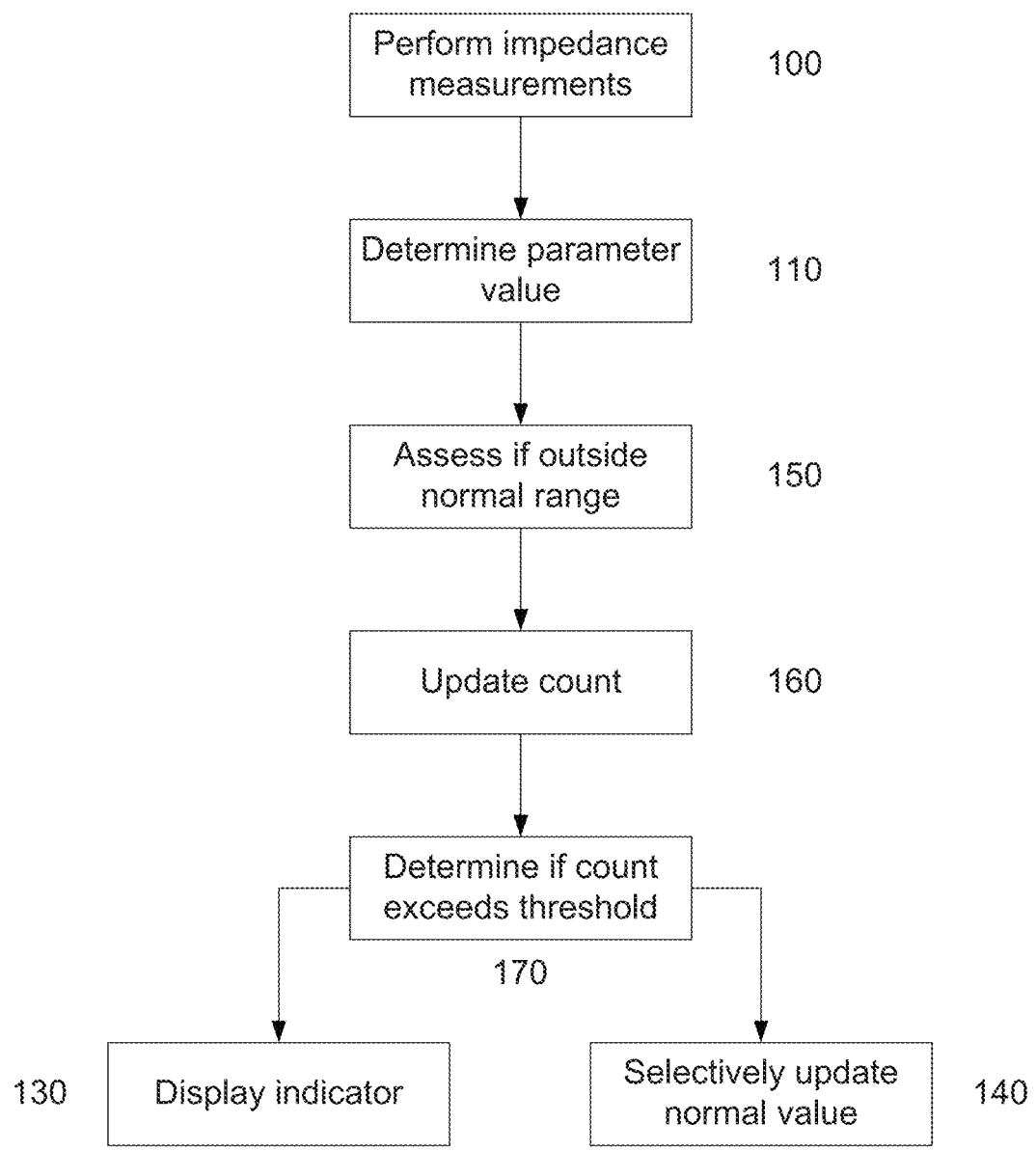
FIG. 1B is a flow chart of a second example of a process for determining an indicator based on measurements of a biological subject.
Figure 2:
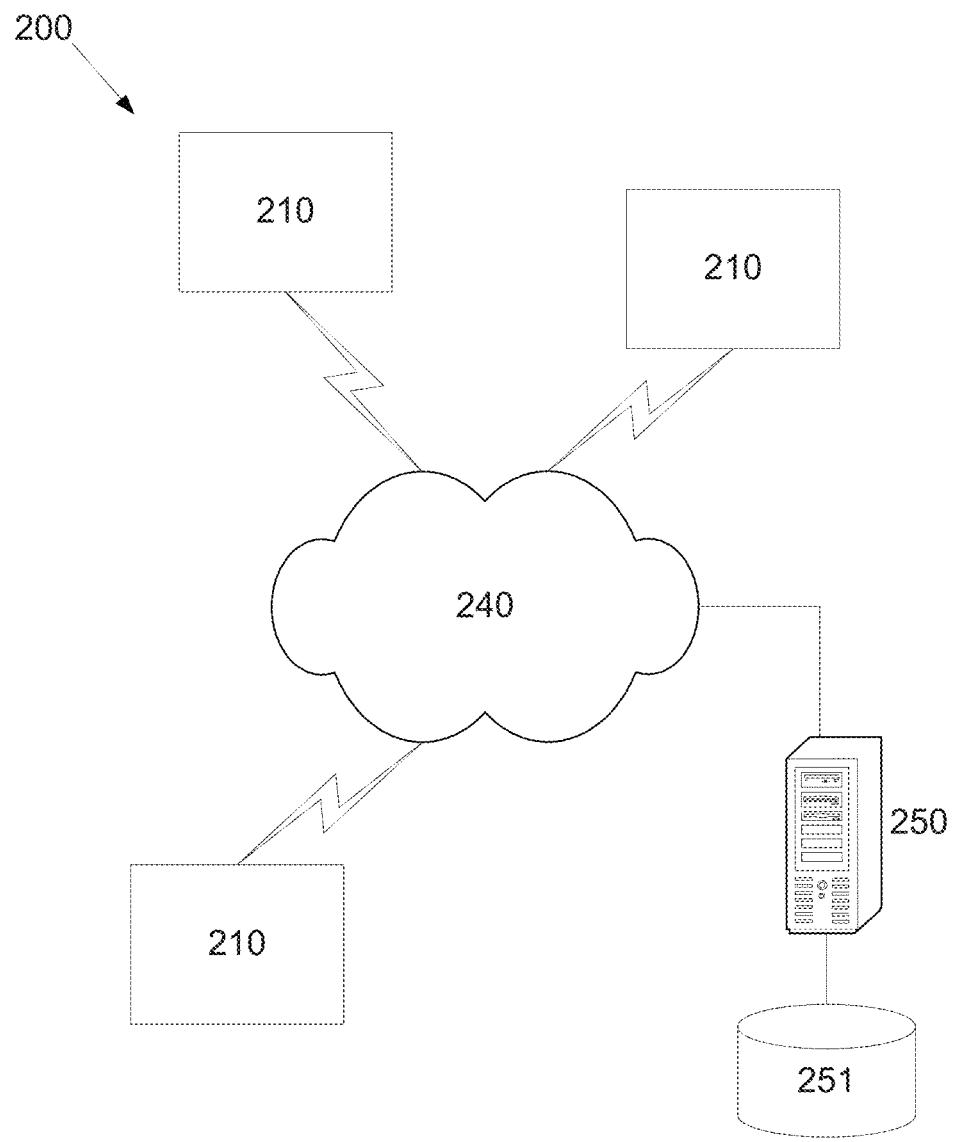
FIG. 2 is a schematic diagram of an example of a distributed system architecture.

In this example, the assessment step 120 of FIG. 1A is performed by comparing the parameter value to a subject normal range to determine if the value falls outside the subject normal range at step 150. Following this, at step 160, a count indicative of a number of parameter values that fall outside the subject normal range is updated, with this being performed depending on results of the determination. For example, if the parameter value falls outside the subject normal range the count can be incremented, whereas if the parameter value falls inside the subject normal range the count could be decremented or reset, depending on the preferred implementation. The count is typically stored in a suitable data repository such as a database or the like, optionally as part of user data associated with the subject. At step 170, it is determined if the count exceeds a threshold, with this being indicative of whether or not the parameter value represents a meaningful change.

In this example, the count is indicative of a number of sequential parameter values that fall outside the subject normal range, with the one or more processing devices operating to reset the count if the parameter value falls inside the subject normal range. In this manner, a meaningful change is identified when a number of sequential measurements fall outside the subject normal range. Alternatively however, the assessment of a meaningful change could be based on other factors, such as how many of a defined number of impedance measurements fall outside the subject normal range, for example if five out of the last ten readings are outside the normal range. Regardless of the approach used, this requires a defined number of parameter values fall outside a range based on a previous subject normal range, before the indicator displayed to the user is updated to reflect a meaningful change, or before the subject normal range is updated, thereby preventing short term variations affecting the displayed indicator or subject normal range.

The nature of the indicator can vary depending on the preferred implementation and the results of the comparison between the count and the threshold. For example, the indicator could be indicative of the parameter value, the subject normal range, a subject normal value, a subject normal parameter value derived from the subject normal range or subject normal value, an indication of whether the parameter value is greater than or lesser than the subject normal range, an indication of whether the parameter value is greater than or lesser than a subject normal parameter value, an indication of whether the parameter value falls outside the subject normal range, an indication of whether the parameter value is greater than or lesser than the subject normal range, a magnitude of a difference between the parameter value and the subject normal range, a magnitude of a difference the parameter value and the subject normal range indicator value, a parameter value change, such as a direction and/or magnitude of the change, a parameter value rate of change or a parameter value trend.

In one specific example, if the count is below the threshold, the indicator is based on the subject normal range or a subject normal value, an indication that there is no meaningful change from the subject normal range or normal value, or a trend indicative of a direction of change of the parameter value relative to the subject normal range or normal value. Alternatively, if the count is above the threshold, the indicator is based on the parameter value or an updated subject normal range or value derived at least in part using one or more parameter values falling outside the previous subject normal range. Thus, it will be appreciated from this that a range of different indicators could be determined and used to display different information to the subject, and/or another user such as a medical practitioner, depending on whether a change is assessed as meaningful. This could include simply indicating that there is no meaningful change from the subject normal value or range, optionally accompanying this with an indication of the current normal value or normal range, or could simply indicate that the indicator is improving or worsening, increasing or decreasing, or the like. Once a meaningful change is identified, the indicator could then reflect this change, for example by basing this on an updated subject normal value or range, current parameter value or the like.

As previously mentioned, the parameter value can be of any appropriate form and could include an impedance value, an impedance parameter value derived from at least one impedance value, such as a value of the impedance at zero or infinite frequency, or could include a body state value derived from either an impedance value or one or more impedance parameter values. For example, the processing device could determine one or more impedance parameter values using an impedance value obtained by performing impedance measurements at a single frequency or a plurality of impedance values obtained by performing impedance measurements at a plurality of frequencies. For example, a single low frequency measurement can be used to approximate $R_0$, which is the resistance at zero frequency, which is in turn indicative of extracellular fluid levels. Other parameters can include $R_\infty$, which is the resistance at infinite frequency, or $Z_c$, which is the resistance at a characteristic frequency. Thus, the impedance values could be measurements of impedance at one or more specific frequencies, with derived impedance parameter values corresponding to measurement of impedance at other frequencies, such as zero or infinite frequencies as will be appreciated by persons skilled in the art.

The parameter value could alternatively be a body state value, which could be indicative of a specific condition, or could be a general indication of a measured body parameter value that is in turn indicative of a condition. Examples include, but are not limited to one or more of Body Composition, Dry Lean Mass, Lean Body Mass, Skeletal Muscle Mass, Segmental Lean Analysis, Body Fat Mass, Segmental Fat Analysis, BMI (Body Mass Index), (Percent Body Fat), Visceral Fat Area, Visceral Fat Level, Total Body Water (TBW), Intracellular Water (ICW), Extracellular Water (ECW), ECW/TBW, Segmental Body Water, Segmental ECW/TBW, Segmental ICW Analysis, Segmental ECW Analysis, Body-Fat-LBM Control, BMR (Basal Metabolic Rate), Leg Lean Mass, TBW/LBM, Whole Body Phase Angle, Segmental Phase Angle, Reactance, Impedance of Each Segment per frequency, or Body Water Composition History. The body state could also be indicative of a general level of health or athletic fitness, such as whether the individual is fit or unfit.

It will be also be appreciated that whilst reference is generally made to a single parameter value, in practice the system could determine one or more indicators based on multiple different parameter values simultaneously.

In one example, the processing device generates a representation using the indicator, and displays the representation on a display, such as a client device screen, as will be described in more detail below. Thus, results could be presented as a graphical representation, for example using a pointer and scale to indicate the magnitude and/or changes in the parameter value, the subject normal range value, differences between the parameter and subject normal range values, or the like. The representation could also include other information, such as an indication of a current count, details of measurement attributes, or the like.

The subject normal range can also be of any appropriate form and could include a subject normal impedance value range, a subject normal parameter value range or a subject normal body status value range. Additionally, multiple subject normal ranges may be provided, so that for example a subject normal range may include a subject normal impedance value range and a subject normal parameter value range. Whilst the subject normal range may be based on an equivalent measure to the parameter value, so that if the parameter value is a value of ECW, the subject normal range could be a range based on values of ECW, this is not essential, and alternatively the subject normal range could be based on a subject normal impedance value which is then used to calculate a subject normal range ECW as required.

The processing device can calculate the parameter value in any appropriate way and this could be performed utilising suitable calculations associated with the particular value to be determined. In one example, a specific equation would be used to calculate each parameter value, for example using equations based on the Cole model discussed in more detail below, or by using specific equations to calculate body composition or other body state indicators, as is known in the art.

As an alternative however, the parameter values could be determined based on a change of impedance from a subject normal value. In this example, a subject normal parameter value and subject normal impedance value can be retrieved, with the measured impedance value being used to establish the difference between the subject normal impedance value and the measured impedance value. This difference is then used to calculate the parameter value. In one example this can be performed using the following equation:

$$PV = B_{PV} + x\Delta I$$

where: PV is the parameter value
$B_{PV}$ is the subject normal parameter value
x is a coefficient
$\Delta I$ is the difference between the subject normal impedance value and the measured impedance value.

The subject normal range can be calculated in any appropriate manner, but typically this is achieved by having the one or more processing devices determine a plurality of parameter values from multiple impedance measurements and then calculate the subject normal range based on these. In one example, the plurality of parameter values are selected ones of multiple parameter values derived from multiple impedance measurements. For example, selected ones of multiple parameter values can be averaged with outlier values being excluded in accordance with normal statistical techniques.

In one particular example, the processing device calculates a subject normal value using one or more of an average of plurality of impedance parameter values, an average of a plurality of parameter values or an average of a plurality of body state values. The one or more processing devices can then calculate the subject normal range based on the subject normal value and a spread of impedance measurements, parameter values or body state values, and/or using a predetermined range from a subject normal range value. In one specific example, the subject normal value is calculated from an average of five parameter values, with the range being based on two or three standard deviations for the five parameter values.

Additionally, and/or alternatively, the subject normal range can also be calculated taking into account details of one or more medical conditions, one or more vital signs or other subject attributes. In this regard, a meaningful change for a fit healthy individual might require a greater change than for a subject suffering from a medical condition, such as heart failure. In this latter case, even minor variations could be indicative of a significant worsening of the condition, and hence would need to be assessed as meaningful, so that the subject or another user is notified of resulting changes.

It will be appreciated from this that multiple different ranges could be set. For example, a first normal range could be set and used to assess the indicator that is displayed to the user, whilst a second normal range could be set to control whether an action, such as generating a medical alert, is performed.

For example, the one or more processing devices can assess if the parameter value falls outside a first subject normal range, selectively update a first count indicative of a number of parameter values falling outside of the first subject normal range, determine if the first count exceeds the first threshold and then displays the indicator based on the determination. Thus, the indicator displayed to the subject or other user is set based on whether or not the first count exceeds the first threshold. Additionally, the processing device can assess if the parameter value falls outside a second subject normal range, selectively update the second count indicative of parameter values that fall outside the second subject normal range, determine if the second count exceeds the second threshold and if so perform an action, such as generating a medical alert, or updating the normal range.

It will be appreciated that the second threshold and second subject normal range can be different to the first subject normal range and first threshold so that for example a greater variation over a shorter duration will result in an action being performed. For example, if a subject's parameter value falls outside the threshold range for five days in a row, an indicator representing a new parameter value could be displayed, with the action only being updated if the parameter value falls outside a broader subject normal range two days in a row. Thus, this could be used to generate an alert in the event that a change in parameter values is indicative of a potentially adverse medical situation, even if the change has not occurred over a sufficiently long duration to be designated a meaningful change. This avoids potentially adverse readings being ignored.

It will also be appreciated from this that the second subject normal range and second threshold could be set depending on the nature of the action to be performed, and that multiple second thresholds and ranges might be defined for different actions. For example, the subject normal range and/or threshold could be larger if the action is to include updating a subject normal range, whereas they could be smaller if the action is to generate a notification of a clinically significant event. The range and threshold could therefore be set taking into account a range of factors, such as details of one or more medical symptoms, one or more vital signs parameter values, one or more subject attributes, or the like.

As an alternative, the processing devices can selectively calculate a new subject normal range in response to user input commands. It will also be appreciated that multiple subject normal ranges could be established so for example an initial subject normal range could be set as a baseline, with a dynamic subject normal range being used to trend variations over shorter time periods. For example, a subject normal range could be updated on a weekly basis with a baseline being used to show a change in a new subject normal range relative to an original starting point.

In one example, the one or more processing devices calculate a parameter value or a subject normal value or range using impedance measurements meeting defined measurement criteria. In particular, this can be used to filter performed impedance measurements so that only impedance measurement meeting defined criteria, and hence measurements that are directly comparable, are used in calculating the subject normal range or the parameter value. This is used to take into account that external factors, such as intake of food or drink, participation in exercise, or the like, can impact on measurements, whilst not representing a fundamental underlying change in the body state of the subject. Thus, this can be used to ensure measurements made at different times of the day, or before and after food or beverages are consumed, are not used in a comparable way.

In order to perform such filtering typically the one or more processing devices determine the measuring attributes and then compare these to defined measurement criteria to determine if the impedance measurements should be used. The measurement attributes can include any one or more of an exercise indicator indicative of participation in exercise, including a type, time or duration of exercise, the time of day, a clothing state, or an indication of consumption of food or beverages, details of one or more medical symptoms, or the like, as well as details of other measured subject parameters, such as a measured weight, a vital sign indicator, such as a skin temperature, body temperature, or heart rate, or the like. For example, an elevated heart rate might indicate that the subject has just finished exercising, which can impact on fluid levels, and hence used to exclude measurements from subject normal range calculations or the like. Accordingly, the criteria are used to ensure impedance measurements to be performed under common conditions, with other measurements not meeting the relevant criteria being excluded as required.

In one specific example the criteria include one or more of: ingesting the same food the day before or at least 8-12 hours before; fasting for 8-12 hours prior to measurement; no alcohol 24 hours prior to measurement; vacating bowels prior to measurement; confirming hydration status prior to measurement through examination of urine colouration; no heavy exercise 24 hours prior to measurement; measurement at same time of day, preferably in the morning; record of menstrual cycle time. An average of multiple measurements might also be required.

As an alternative to ignoring or using measurements, measurement attributes can also be used to modify measurements, thereby allowing the measurements to be used, whilst taking into account that changes in measurement attributes compared to the defined criteria, could influence in the measurement. In this example, the measurement attributes can be compared to defined measurement criteria with results of the comparison being used to determine a compensation factor, which is then used to selectively modify an impedance value indicative of a measured impedance, or an impedance parameter value derived from at least one impedance value or a body state value derived from an impedance value or parameter value. It will be appreciated that such compensation can be useful in allowing the measurement to be used, but that the respective measurement could be flagged so the manner in which the measurement is used can be controlled. For example, this could be excluded from use in calculating normal ranges, but still used to allow an indictor to be displayed. The compensation factor can be determined in any one of a number of ways and could be derived through experimentation on a sample population, or based on previous measurements for the subject. For example, this could be used to modify a TBW measurement performed at a different time of day, thereby compensating for known changes in hydration throughout the day.

It will be appreciated that in a similar manner a compensation factor can be based on known measurement errors associated with the device as well as physiological errors that can be calculated using repeated measurements and testing in a laboratory.

The system can also be adapted to examine trends for the subject, corresponding to particular changes in parameter values, impedance values or body state value over time. Trending can be used to assist in assessing whether changes in a parameter value and significant and/or heading in a desired direction, and/or could be used for predictive purpose, for example to assess the likely time at which the user will reach a desired end goal.

In this instance, the one or more processing devices can determine at least one parameter value change using multiple parameter values and then selectively use the parameter value change to determine a parameter value trend indicative of a direction of parameter value change, a rate of parameter value change or a magnitude of parameter value change.

In order to achieve this, the one or more processing devices can compare the parameter value change to a change threshold and selectively determine the parameter value trend based on results of the comparison, so that for example a trend will only be established if the change or rate of change exceeds a defined threshold.

The change in parameter values could be established over sequential parameter values, could be based on a current parameter value and a normal parameter value or could be based on a current parameter value and an nth previous parameter value. For example, this could involve looking at an overall change between 1st and 10th measurements, or a current measurement and how this differs from a most recently established normal. This could also be determined based on multiple measurements, for example by performing a regression analysis, such as a linear regression and then examining a gradient of the resulting slope, to determine whether a parameter value is trending upwards or downwards, and the rate at which this occurs.

Once a trend has been identified, this could be used to predict a future parameter value, a future subject normal value, a future subject normal range or a time needed to reach a target. For example the trend and rate of change could be extrapolated in order to predict a likely future value and when this will occur. Examination of the subject normal range and/or variability of measurements could then be used to assess when a new subject normal value and/or range is likely to established, and the corresponding values these are likely to have.

The trend could also be used to generate an indicator, for example to show that the parameter value is heading in a particular upward or downward direction, and also to indicate whether this is happening quickly or slowly, for example based on comparison of a slope gradient to a threshold.

In one example, the process is performed using a measurement system that performs impedance measurements and provides an indication of at least one measured impedance to the one or more processing devices via a communications network. The measurement system can be of any appropriate form and could include a measuring device and a client device communication with the measuring device. The use of a separate client device allows a user's device such a mobile phone, smart phone, table or the like to be used in conjunction with the measuring device thereby reducing processing requirements for the measuring device. The client device can receive measurement data indicative of an impedance measurement performed on the subject and then provide subject data to one or more processing devices with the subject data including any one or more of the user identifier associated with the user, the measurement data, one or more measurement impedance values, one or more parameter values, one or more vital sign values, and one or more measurement attributes.

In one particular example, the user identifier can be used to retrieve previously stored information, such as to access a user profile including any one or more of previous impedance measurements or parameter values, subject normal ranges, predetermined criteria, defined thresholds, actions to be performed, or the like.

The vital signs indicator can include a cardiac parameter value, a respiratory parameter value, a blood potassium level, a temperature, a blood pressure, a respiratory rate, a heart rate and blood oxygenation level. It will be appreciated however that any vital sign indicators could also be recorded and used.

In one example, the measuring device includes a signal generator electrically connected to drive electrodes to apply drive signal to a user, a sensor electrically connected to sense electrodes to measure a response signal in the user and a measuring device processor that at least in part controls the signal general, receives an indication of a measured response signal from the sensor and generates a measurement data indicative of at least one measured impedance value.

As previously mentioned, the above described process can be performed for other measurements more generally. In this instance the one or more processing devices typically determine a parameter value at least in part using results of at least one measurement, retrieve a subject normal range derived from results of a plurality of previous measurements performed on the subject, determine if the parameter value falls outside a subject normal range, the subject normal range being at least partially based on the subject normal range, update a count indicative of a number of parameter values that fall outside the subject normal range depending on results of the determination, determine if the count exceeds a threshold and generate the indicator at least in part based on whether the count exceeds the threshold.

It will be appreciated that the system could be used solely for updating a subject normal range, and displaying an indicator is not necessarily essential.

The system can alternatively be adapted to select whether measurements should be used, ignored, or modified, for example if defined criteria are not met. In this case, the processing devices determine a parameter value at least in part using results of the at least one impedance measurement, determine measurement attributes associated with at least one impedance measurement, compare the measurement attributes to defined measurement criteria if the measurement criteria meet the defined criteria obtain a subject normal range derived from results of a plurality of previous impedance measurements performed on the subject, determine if the parameter value falls outside a subject normal range, the subject normal range being at least partially based on the subject normal range, display an indicator at least partially based on the result of the determination or if the measurement criteria do not meet the defined criteria, display an indicator based on the parameter value. Alternatively, a compensation factor can be determined in accordance with results of the comparison, with the compensation factor being used to selectively modify at least one of an impedance value indicative of a measured impedance, an impedance parameter value derived from at least one impedance value and a body state value derived from at least one impedance value or at least one impedance parameter value. Again this could be performed for a measurement other than an impedance measurement in a similar manner.

Although not essential, in one example, the above described process is implemented using a distributed architecture including one or more measuring systems in communication with one or more processing devices. An example system will now be described with reference to FIGS. 2 to 5.

In this example, the system 200 includes a number of measuring systems 210 coupled via a communications network 240 to one or more other measuring systems 210 and/or one or more processing devices, such as a server 250, which may in turn be coupled to a database 251. This arrangement allows data from performed measurements to be collected by the measurement systems 210 and provided to the server 250 for analysis. Collected data may also be stored in the database 251 together with resulting reference signatures and/or heart failure indicators, allowing this information to be remotely accessed and viewed by third parties, such as clinicians, or the like.

In the above arrangement, the communications network 240 can be of any appropriate form, such as the Internet and/or a number of local area networks (LANs) and provides connectivity between the measuring systems 210 and the server 250. It will however be appreciated that this configuration is for the purpose of example only, and in practice the measuring systems 210 and server 250 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

It will also be noted that the use of the distributed system is purely optional and the process can be implemented using a standalone measuring system.

Figure 3A:
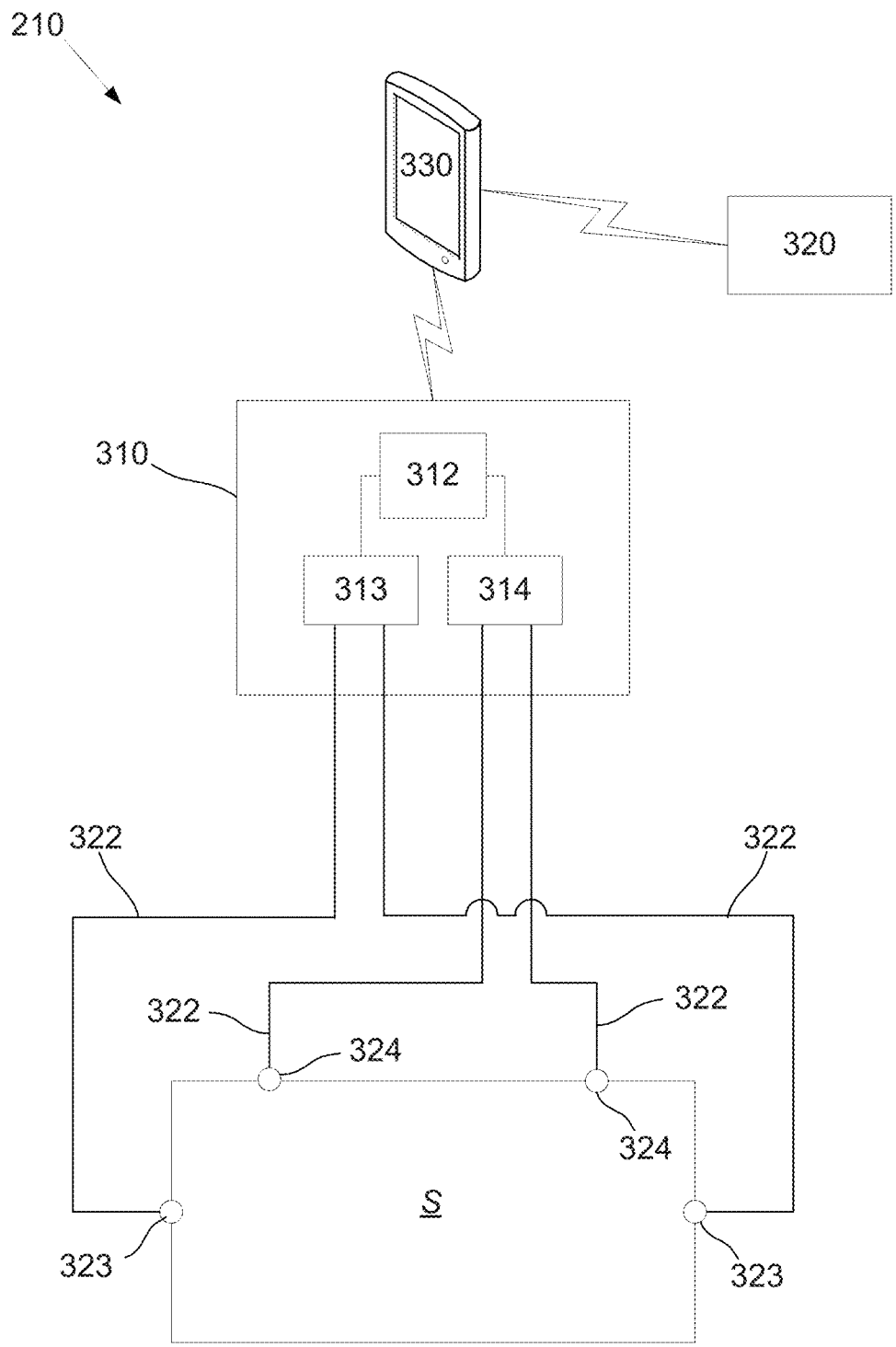
FIG. 3A is a schematic diagram of a measuring system.

An example measuring system will now be described in further detail with reference to FIG. 3A.

In this example, the measuring system includes an impedance measuring unit having an impedance measuring device 310, which is in turn in communication with a processing system in the form of a client device 330, such as a portable computer system, mobile phone, tablet or the like. One or more optional physical characteristic sensors 320 can also be provided for capturing information regarding physical characteristics of an individual/subject.

The nature of the physical characteristic sensors 320 will vary depending on the characteristics to be measured, and could include for example scales for measuring an individual/subject's weight and/or an image capture device, such as a camera, body scanner, DEXA (Dual-Energy X-ray Absorptiometry), 3D laser or optical scanning, or the like, for measuring a height and/or body segment dimensions, as will be described in more detail below. Additionally or alternatively, this could include electronic scales for measuring a weight, and other monitoring equipment, for example for measuring heart rate, blood pressure or other characteristics.

The impedance measuring device 310 typically includes a measuring device processor 312 coupled to at least one signal generator 313 and at least one sensor 314, which are in turn coupled to respective drive and sense electrodes 323 and 324, via leads 322. In use, the signal generator 313 generates a drive signal, which is applied to the individual/subject S via the drive electrodes 323, whilst the sensor 314 measures a response signal via the sense electrodes 324. In use, the measuring device processor 312 controls the at least one signal generator 313 and the at least one sensor 314, allowing the impedance measurements to be performed.

In particular, the measuring device processor 312 is adapted to generate control signals, which cause the signal generator 313 to generate one or more alternating signals, such as voltage or current signals of an appropriate waveform, which can be applied to a subject S, via the first electrodes 323 and processing received signals from the sensor 314. It will be appreciated that the measuring device processor 312 may be any form of electronic processing device capable of performing appropriate control, and could include an FPGA (field programmable gate array), or a combination of a programmed computer system and specialised hardware, or the like.

The signal generator 313 could be of any appropriate form, but will typically include digital to analogue converters (DACs) for converting digital signals from the processing device to analogue signals, which are amplified to generate the required drive signals, whilst the sensor 314 typically includes one or more amplifiers for amplifying sensed response signals and analogue to digital converters (ADCs) to digitise the analogue response signals and providing digitised response signals to the processing device.

The nature of the alternating drive signal will vary depending on the nature of the measuring device and the subsequent analysis being performed. For example, the system can use Bioimpedance Analysis (BIA) in which a single low frequency signal is injected into the subject S, with the measured impedance being used directly in the determination of biological parameters. In one example, the applied signal has a relatively low frequency, such as below 100 kHz, more typically below 50 kHz and more preferably below 10 kHz. In this instance, such low frequency signals can be used as an estimate of the impedance at zero applied frequency, commonly referred to as the impedance parameter value $R_0$, which is in turn indicative of extracellular fluid levels.

Alternatively, the applied signal can have a relatively high frequency, such as above 200 kHz, and more typically above 500 kHz, or 1000 kHz. In this instance, such high frequency signals can be used as an estimate of the impedance at infinite applied frequency, commonly referred to as the impedance parameter value $R_\infty$, which is in turn indicative of a combination of the extracellular and intracellular fluid levels, as will be described in more detail below.

Alternatively and/or additionally, the system can use Bioimpedance Spectroscopy (BIS) in which impedance measurements are performed at each of a number of frequencies ranging from very low frequencies (1 kHz and more typically 3 kHz) to higher frequencies (1000 kHz), and can use as many as 256 or more different frequencies within this range. Such measurements can be performed by applying a signal which is a superposition of plurality of frequencies simultaneously, or a number of alternating signals at different frequencies sequentially, depending on the preferred implementation. The frequency or frequency range of the applied signals may also depend on the analysis being performed.

When impedance measurements are made at multiple frequencies, these can be used to derive one or more impedance parameter values, such as values of $R_0$, $Z_c$, $R_\infty$, which correspond to the impedance at zero, characteristic and infinite frequencies. These can in turn be used to determine information regarding both intracellular and extracellular fluid levels, as will be described in more detail below.

A further alternative is for the system to use Multiple Frequency Bioimpedance Analysis (MFBIA) in which multiple signals, each having a respective frequency are injected into the subject S, with the measured impedances being used in the assessment of fluid levels. In one example, four frequencies can be used, with the resulting impedance measurements at each frequency being used to derive impedance parameter values, for example by fitting the measured impedance values to a Cole model, as will be described in more detail below. Alternatively, the impedance measurements at each frequency may be used individually or in combination.

Thus, the measuring device 310 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically arranged, with two signal generators 313 being independently controllable, to allow the signal voltage across the subject to be varied, for example to minimise a common mode signal and hence substantially eliminate any imbalance as described in patent application number WO2009059351.

As the drive signals are applied to the subject, the sensor 314 then determines the response signal in the form of the voltage across or current through the subject S, using second electrodes 324. Thus, a voltage difference and/or current is measured between the second electrodes 324. In one example, a voltage is measured differentially, meaning that two sensors 314 are used, with each sensor 314 being used to measure the voltage at each second electrode 324 and therefore need only measure half of the voltage as compared to a single ended system. Digitised response signals are then provided to the measuring device processor 312, which determines an indication of the applied drive signal and measured response signals, and optionally uses this information to determine measured impedances.

Thus, in the above arrangement, four electrodes are shown, with two forming drive electrodes and two forming sense electrodes. However, this is not essential, and any suitable number of electrodes could be used. Furthermore, a single signal generator and sensor are shown, but again a respective signal generator and sensor could be used for each drive and sense electrode, respectively, and the described arrangement is for the purpose of illustration only.

Figure 3B:
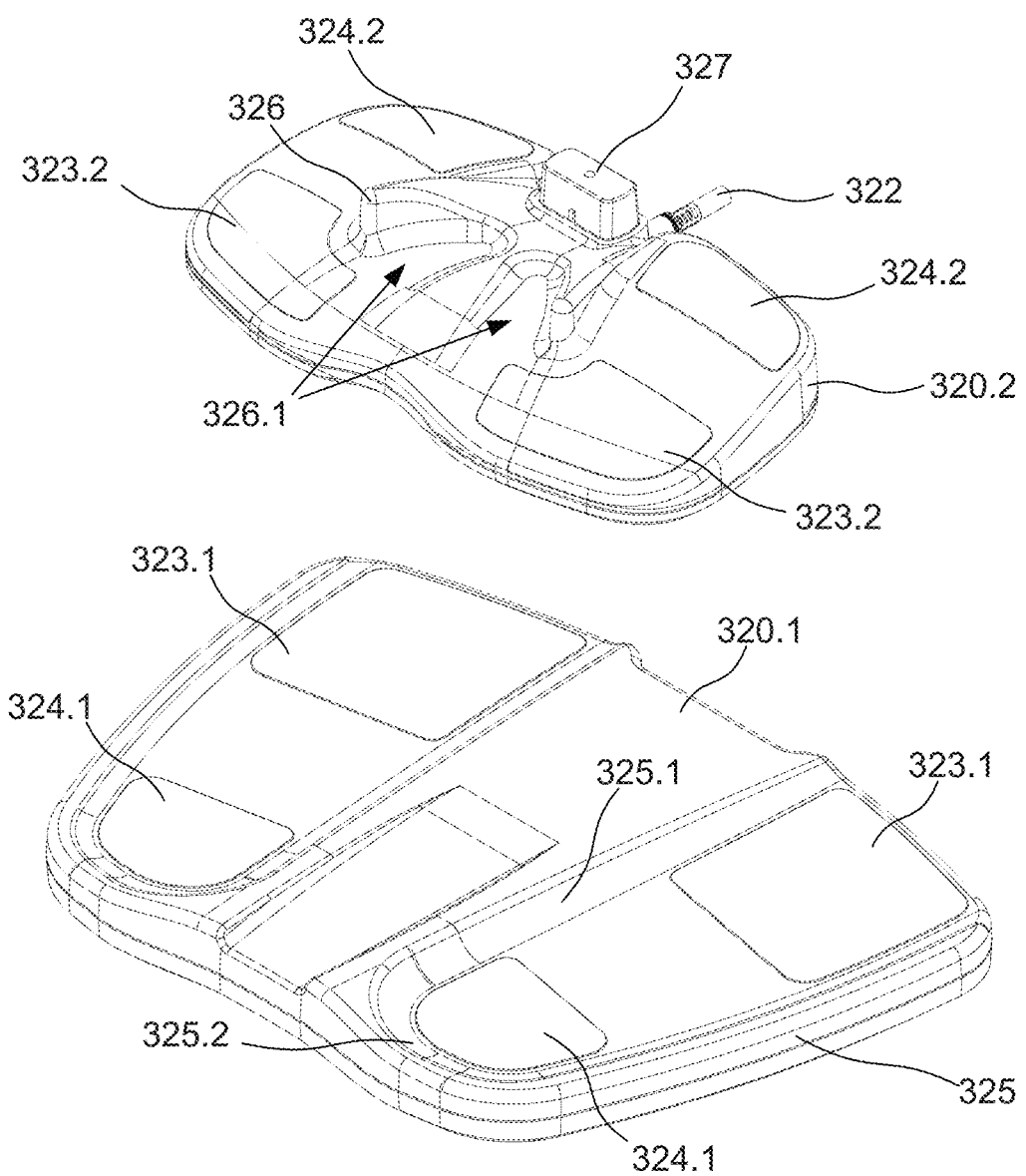
FIG. 3B is a schematic diagram of a specific example of the physical construction of the impedance measuring device of FIG. 3A.

A further example of a physical construction of the measuring device is shown in FIG. 3B.

In this example, the measuring device includes first and second housings 320.1, 320.2. The first housing 320.1 has a form factor similar to a set of scales, and includes a generally rectangular body having two spaced pairs of foot drive and sense electrodes 323.1, 324.1 formed from spaced apart metal plates provided on an upper surface, thereby forming footplates on which a user can stand. The second housing 320.2 has a generally rectangular body having two spaced pairs of hand drive and sense electrodes 323.2, 324.2 formed from spaced apart metal plates provided on an upper surface, thereby forming handplates on which a user can rest their hands.

The first housing 320.1 includes a raised section 325, defining a lip 325.1 extending at least partially around each pair of foot drive and sense electrodes to thereby guide positioning of a subject's foot relative to the foot drive and sense electrodes in use. In particular, the raised lip 325.1 includes a rear portion 325.2 configured to engage at least a heel of the user. A similar effect is achieved for the second housing by having a raised portion 326 positioned between each pair of hand drive and sense electrodes, the raised portion defining thumb recesses 326.1 to thereby guide positioning of a subject's thumbs, with the crook of the thumb engaging the raised portion, and hence hands relative to each pair of hand drive and sense electrodes in use.

In this regard, it will be appreciated that whilst this will still allow for some minor variation in positioning between different individuals, for example due to different feet and hand sizes, this helps ensure that any given user's hands and feet are provided at a consistent position relative to the drive and sense electrodes each time the apparatus is used. This provides reproducible positioning, which in turn reduces variations between successive measurements that could be caused by changes in hand or foot position.

This arrangement allows the unit to be used by having the user stand on the first housing, or alternatively sit on a chair, with their feet resting on the foot drive and sense electrodes. The user can then place their hands on the hand drive and sense electrodes on second housing, which can be supported by a desk or table in a seated arrangement, or by a stand or other support for a standing arrangement.

The use of two housing containing separate electrodes, therefore allows impedance measurements to be performed in a variety of circumstances, and in particular allows measurements to be performed in either seated or standing arrangements, which is important in ensuring the system can be used by individuals having restricted physical capabilities. Additionally, the use of metal plate electrodes provided in a housing allows the system to be readily used, and avoids the need for preparation, such as cleaning of tissue surfaces or removal of hair, to allow wet electrodes to be applied to the skin.

In the above arrangement, the client device 330 is in communication with the measuring device processor 312, typically via a wireless communications channels, such as Bluetooth or the like. In one example, the client device 330 is provided in a stand, which is then attached to mounting 327, allowing the client device 330 to be supported on the apparatus in use. This allows the client device 330 to act as a user interface, allowing operation of the impedance measuring device to be controlled, and allowing results of impedance measurements to be displayed.

In particular, the client device 330 can be used to instruct the measuring device processor 312 on a particular sequence of impedance measurements that need to be performed, further receiving either an indication of the drive/sense signals and/or measured impedance values. The client device 330 can then optionally perform further processing, for example to determine the impedance indicators, although alternatively this may not be required and raw impedance data could be provided to the server 250 for analysis.

The client device 330 can also combine impedance values or indicators with information regarding indications of heart failure states and physical characteristics determined either by manual user input or based on signals from one or more physical characteristic sensors. This allows the client device to generate the reference data, which is then transferred via the communications network 240 to the server 250. However, alternatively, the server 250 could obtain the indication of heart failure states and/or physical characteristic from other data sources, depending on the preferred implementation.

Figure 4:
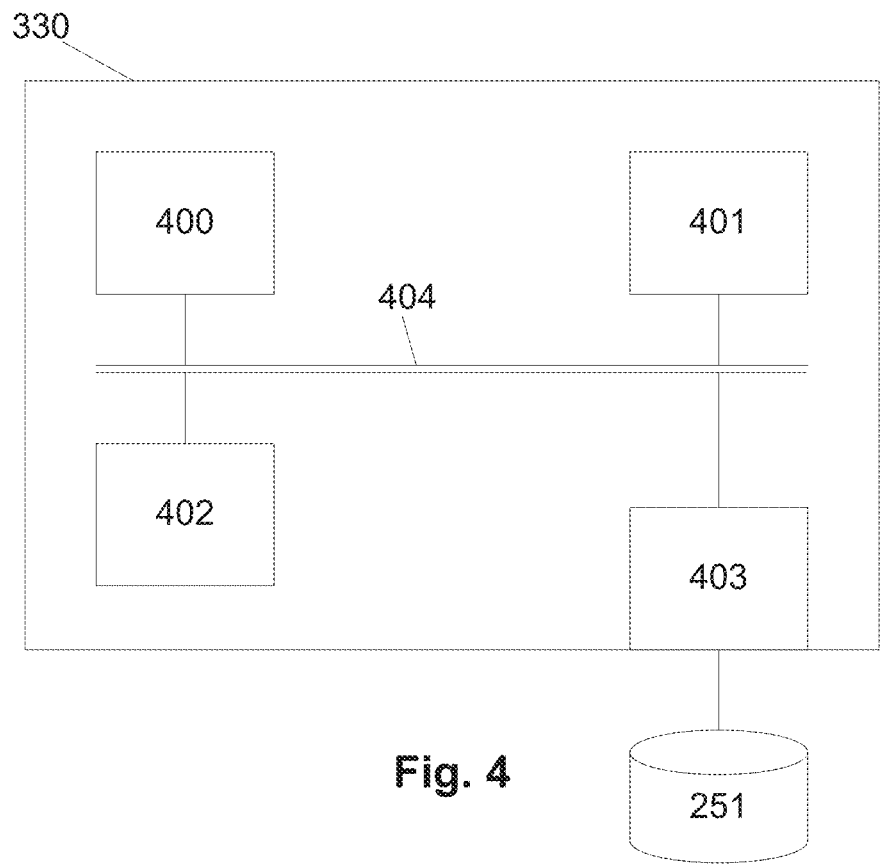
FIG. 4 is a schematic diagram of an example of a client device.

Accordingly, it will be appreciated that the client device 330 can be of any appropriate form and one example is shown in FIG. 4. In this example, the client device 330 includes at least one microprocessor 400, a memory 401, an input/output device 402, such as a keyboard and/or display, and an external interface 403, interconnected via a bus 404 as shown. The external interface 403 can be utilised for connecting the client device 330 to peripheral devices, such as the communications networks 240, databases, other storage devices, or the like. Although a single external interface 403 is shown, this is for the purpose of example only, and in practice multiple interfaces using various methods (eg. Ethernet, serial, USB, wireless or the like) may be provided.

In use, the microprocessor 400 executes instructions in the form of applications software stored in the memory 401 to allow communication with the server 250, for example to allow reference data to be provided to the sever, or the like.

Accordingly, it will be appreciated that the client device 330 may be formed from any suitable processing system, such as a suitably programmed PC, Internet terminal, laptop, or hand-held PC, and in one preferred example is either a tablet, or smart phone, or the like. Thus, in one example, the client device 330 is a standard processing system such as an Intel Architecture based processing system, which executes software applications stored on non-volatile (e.g., hard disk) storage, although this is not essential. However, it will also be understood that the client devices 330 can be any electronic processing device such as a microprocessor, microchip processor, logic gate configuration, firmware optionally associated with implementing logic such as an FPGA (Field Programmable Gate Array), or any other electronic device, system or arrangement.

Figure 5:
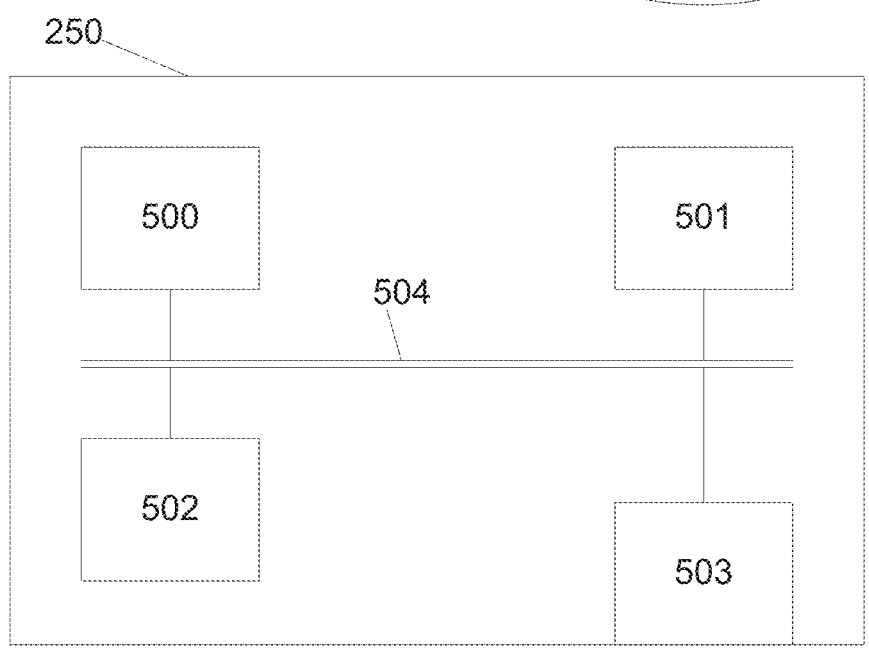
FIG. 5 is a schematic diagram of an example of a server.

An example of a suitable server 250 is shown in FIG. 5. In this example, the server includes at least one microprocessor 500, a memory 501, an optional input/output device 502, such as a keyboard and/or display, and an external interface 503, interconnected via a bus 504 as shown. In this example the external interface 503 can be utilised for connecting the server 250 to peripheral devices, such as the communications networks 240, databases 251, other storage devices, or the like. Although a single external interface 503 is shown, this is for the purpose of example only, and in practice multiple interfaces using various methods (eg. Ethernet, serial, USB, wireless or the like) may be provided.

In use, the microprocessor 500 executes instructions in the form of applications software stored in the memory 501 to allow the required processes to be performed, including communicating with the client devices 330, and optionally receiving, analysing and/or displaying results of impedance measurements. The applications software may include one or more software modules, and may be executed in a suitable execution environment, such as an operating system environment, or the like.

Accordingly, it will be appreciated that the server 250 may be formed from any suitable processing system, such as a suitably programmed client device, PC, web server, network server, or the like. In one particular example, the server 250 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement. Accordingly, whilst the term server is used, this is for the purpose of example only and is not intended to be limiting.

Whilst the server 250 is a shown as a single entity, it will be appreciated that the server 250 can be distributed over a number of geographically separate locations, for example by using processing systems and/or databases 251 that are provided as part of a cloud based environment. Thus, the above described arrangement is not essential and other suitable configurations could be used.

However, it will be appreciated that the above described configuration assumed for the purpose of the following examples is not essential, and numerous other configurations may be used. It will also be appreciated that the partitioning of functionality between the measuring device 310, client devices 330, and servers 250 may vary, depending on the particular implementation.

Figure 6A:
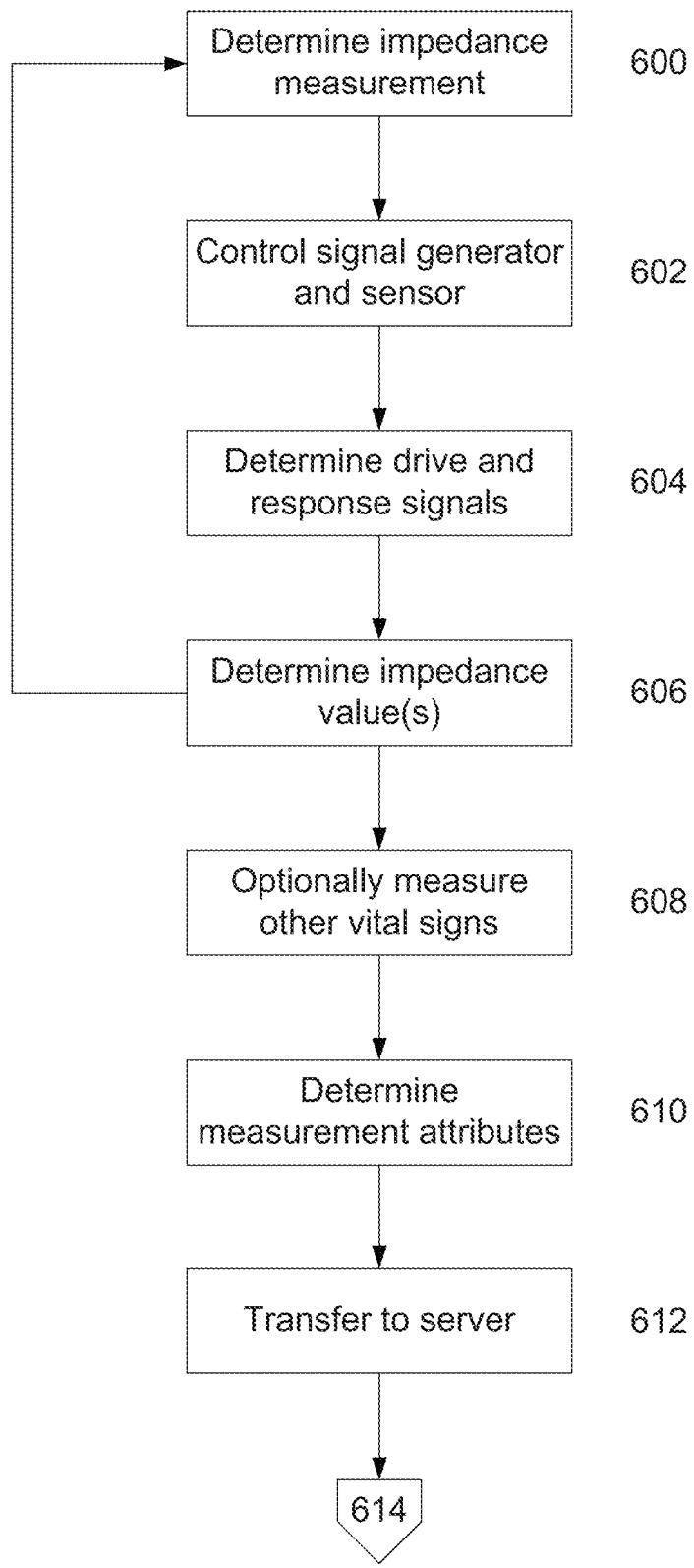
FIGS. 6A to 6C are a flow chart of a further example of a method of determining an indicator based on measurements of a biological subject.
Figure 6B:
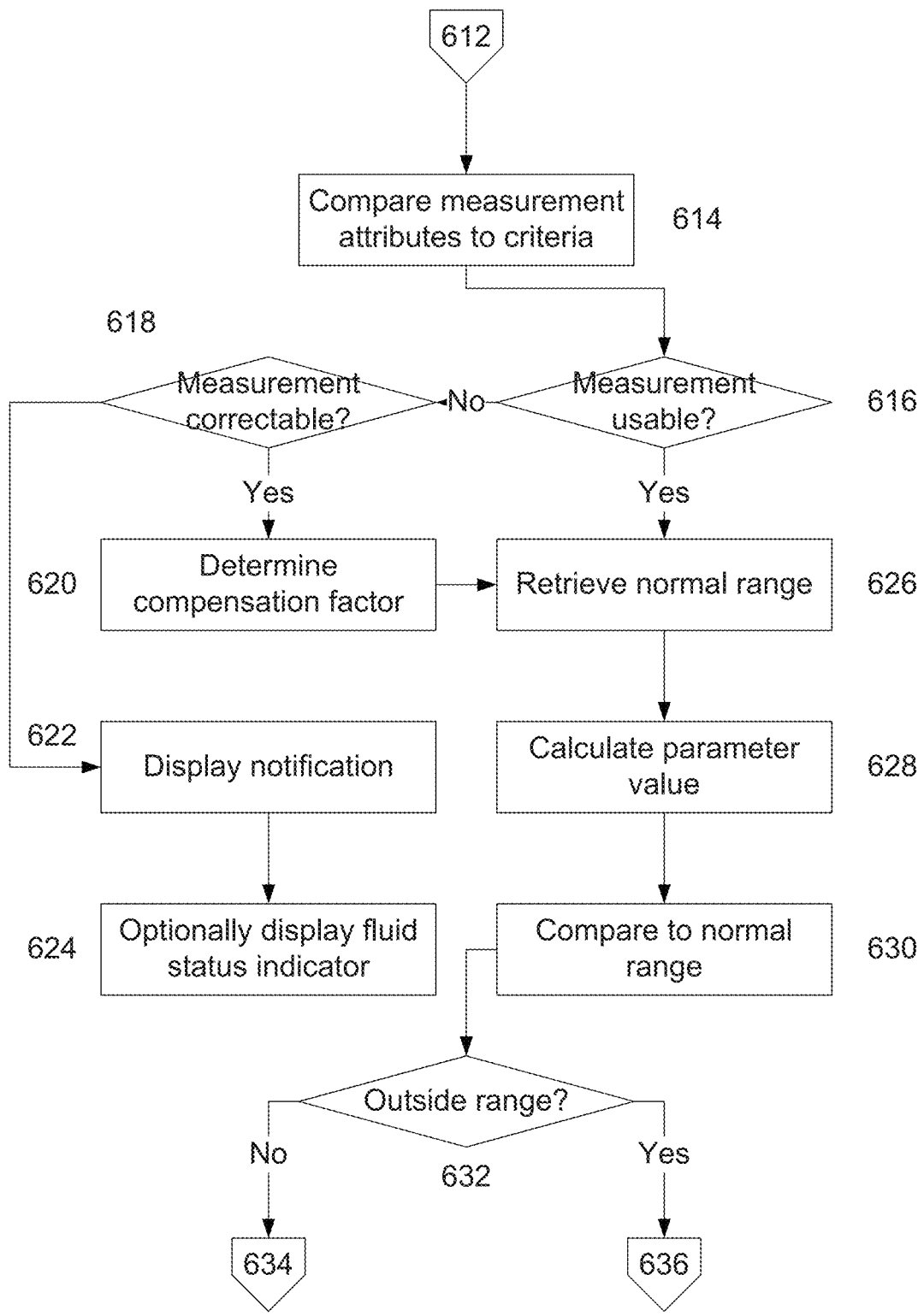
Figure 6C:
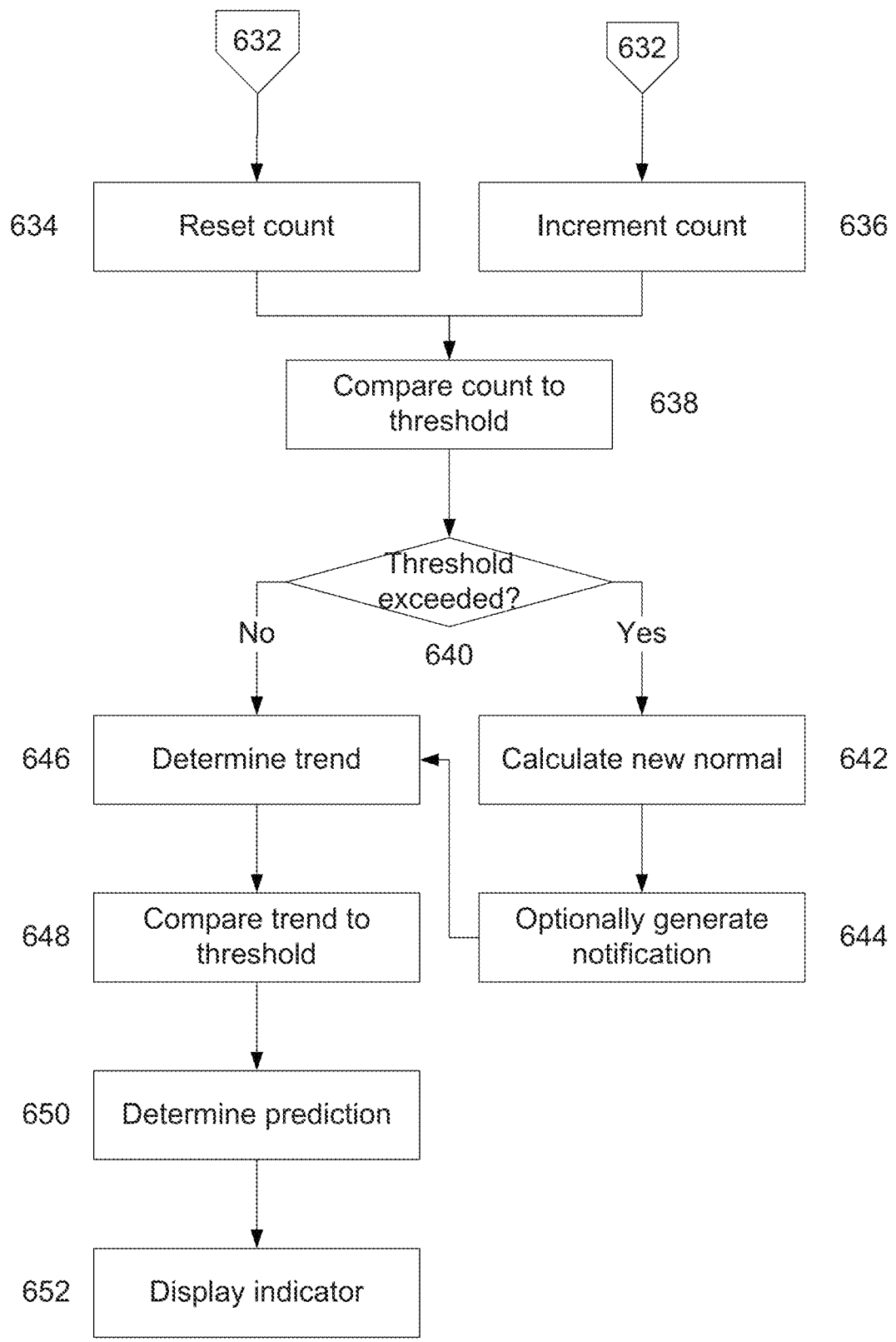

Operation of the system will now be described in further detail with reference to FIGS. 6A to 6C. Throughout the following example reference will be made to a user. In this regard, the user will generally be understood to include the subject, but may also encompass an individual assisting the subject in performing the measurement, such as a medical practitioner or the like.

For the purpose of these examples it will also be assumed that a user uses the client device 330 to control the measuring device 310 and any characteristics sensors, allowing impedance measurements to be performed and optionally allowing information regarding physical characteristics to be collected. This is typically achieved by having the user interact with the system via a GUI (Graphical User Interface), or the like presented on the client device 330, which may be generated by a local application, or hosted by the server 250, which is typically part of a cloud based environment, and displayed via a suitable application, such as a browser or the like, executed by the client device 330. Actions performed by the client device 330 are typically performed by the processor 400 in accordance with instructions stored as applications software in the memory 401 and/or input commands received from a user via the I/O device 402. Similarly, actions performed by the server 250 are performed by the processor 500 in accordance with instructions stored as applications software in the memory 501 and/or input commands received from a user via the I/O device 502, or commands received from the client device 330.

In this example, at step 600, the measuring device processor 312 determines the impedance measurement to be performed. This can be achieved in any suitable manner, but would typically include having the user selecting one of a number of available measuring procedures presented on the client device 330, with the client device 330 generating instructions which are provided to the measuring device processor 312.

Prior to a measurement being performed, the first and second electrodes 323, 324 are provided in contact with the subject to allow one or more signals to be injected into the subject S, and allowing a response signal to be measured. The location of the electrodes 323, 324 will depend on the segment of the subject S under study. Thus, for example, the electrodes 323, 324 can be placed on the thoracic and neck region of the subject S to allow the impedance of the chest cavity to be determined. Alternatively, positioning electrodes on the wrist and ankles of a subject allows the impedance of limbs, torso and/or the entire body to be determined. In one example, the general arrangement is to provide electrodes on the hand at the base of the knuckles and between the bony protuberances of the wrist, and on the feet at the base of the toes and at the front of the ankle.

In the arrangement of FIG. 3B, prior to the measurement being performed the subject stands on the first housing 320.1, or alternatively sits on a chair, with their feet resting on the foot drive and sense electrodes 323.1, 324.1. The user then places their hands on the hand drive and sense electrodes 323.2, 324.2 on the second housing 320.2, which can be supported by a desk or table in a seated arrangement, or by a stand or other support for a standing arrangement.

Figure 8A:
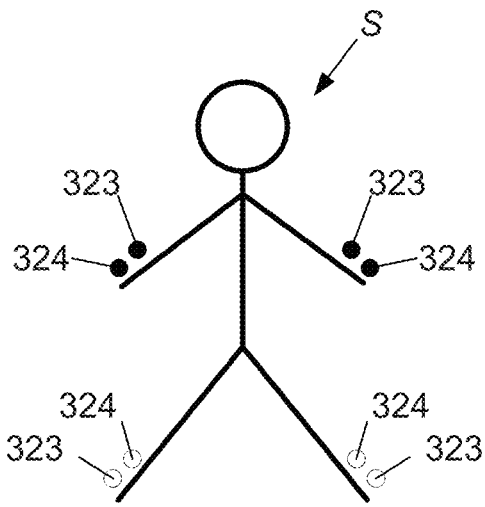
FIGS. 8A to 8E are schematic diagrams of examples of electrode positions for use in performing impedance measurements.
Figure 8B:
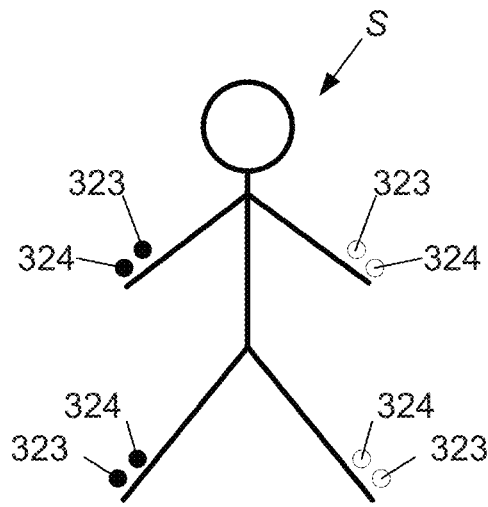
Figure 8C:
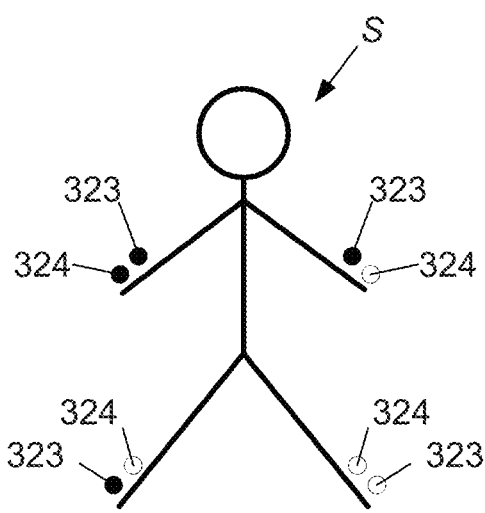
Figure 8D:
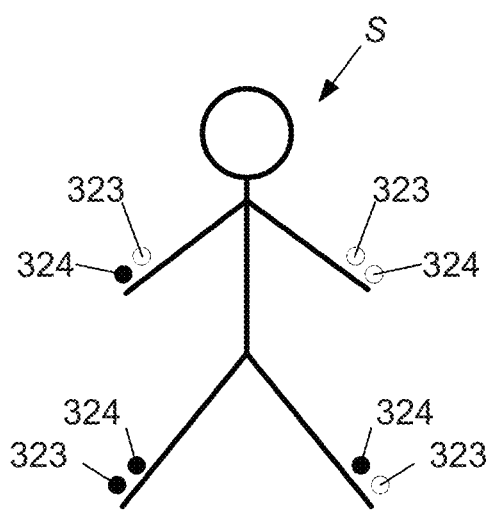
Figure 8E:
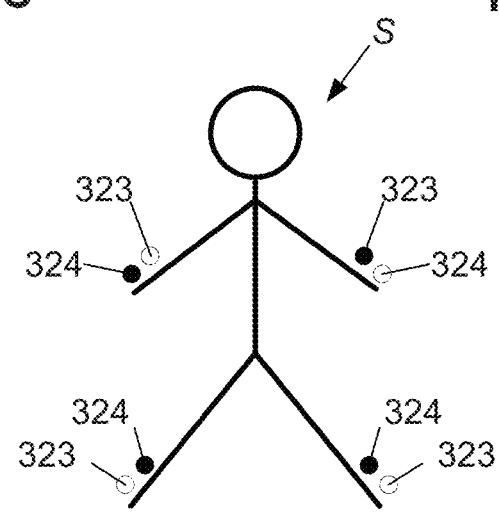

The configuration shown in FIG. 8A can then be used to allow torso measurements to be performed, whilst the configurations shown in FIGS. 8B, 8C, 8D and 8E can be used to allow right whole of body, right arm, right leg and left torso to be measured respectively. Once electrodes are positioned, the operator activates the impedance measurement process, causing a sequence of drive signals to be applied to the subject at multiple frequencies.

At step 602, the measuring device processor 312 controls the signal generator and sensor, causing the drive signals to be applied to the individual/subject and causing the corresponding response signals to be measured, allowing the measuring device processor 312 to determine both the drive and response signals at step 604.

In this regard, the response signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

At step 606, the drive and response signals are used to determine an impedance value. This can be performed by the measuring device 310 alone, or can be performed in conjunction with the client device 330, for example by transferring measured current and voltage signals to the client device 330, which then analyses these to determine the measured impedances.

In the case of BIS, impedance or admittance measurements are determined from the signals at each frequency by comparing the recorded voltage and the current through the subject. The demodulation algorithm can then produce amplitude and phase signals at each frequency, allowing an impedance value at each frequency to be determined.

The above described process can be performed multiple times, for example to allow impedance measurements to be determined for multiple body segments, including the torso and one or more other segments, such as limbs. Additionally or alternatively, the process may be performed multiple times for the same body segment, with an average (or other statistical measure, such as median, mode, or the like) of two or more measurements being determined and, for example, used for further analysis.

At step 608, one or more vital signs and/or one or more other body parameters could optionally be measured. This could include any one or more of a weight, a cardiac parameter value such as a heart rate, a respiratory parameter value such as a breathing rate, a blood potassium level, a temperature, a blood pressure, a blood oxygenation level, or the like. This information could be determined manually, for example by having a clinician manually input measurement values using an interface presented on the client device 330, or could be performed by having the client device 330 acquire measurements from suitable sensors.

At step 610, one or more measurement attributes are determined. The measurement attributes will be determined by the client device 330 in a variety of manners depending on the nature of the attributes. Example attributes can include a time of day, a clothing state, a consumption of feed or beverage, details of one or more medical symptoms, as well as body parameters as measured above. Thus, attributes such as the time of day can be measured automatically by the client device, whereas other attributes may need to be provided manually by the user, for example by having the user provide appropriate inputs via a user interface presented on the client device 330. This could be achieved in any appropriate manner, such as by asking the user a series of standard questions, with answers to the questions being used to establish the measurement attributes.

As will be described below, the measurement attributes are used to determine if measurement criteria are met. In particular, the measurement criteria are used to establish that different measurements have been performed in a consistent manner. Accordingly, as an alternative to determining actual measurement attributes, the approach could alternatively involve having the user confirm a standard set of measurement attributes apply in the current situation. In one example, this is performed as part of the measurement process selection, by having the user initially select a particular measurement process, with it being inherent in this selection that the measurement attributes meet the criteria. For example, the user could select between "standard measurement" and "non-standard measurement" options, with the standard measurement option being selected if the measurement attributes will meet the criteria.

At step 612 subject data, including results of any measurements, any measurement attributes and a user identifier, is created and uploaded to the server 250 for analysis. The user identifier is used to retrieve user data, such as a user profile, or the like, which is in turn used to determine measurement criteria.

In this regard, as previously mentioned, to ensure measurements are usable the measurements must meet particular criteria. Whilst the criteria can be prescribed, in some circumstances it is merely sufficient for measurements to be performed in a consistent manner each time, meaning this does not need to be consistent between different users, but must be similar for each user. In this case, the user can establish a set of criteria during an initial measurement, with this being stored as part of the user data, and with attributes of subsequent measurements being compared to these criteria to assess whether a measurement is usable. This may take into account a time of day at which the measurement is performed, a clothes state and information regarding consumption of alcohol, caffeine or other food and drink that could adversely impact a fluid status, recent exercise, or the like.

The measurement attributes are therefore compared to the criteria at step 614 to determine if the measurement is usable at step 616. If the measurement is not usable for any reason, such as if the criteria are not met, the server 250 can determine if the measurement is correctable at step 618. In this regard, for some measurement attributes a predictable change may occur if the criteria is not met, allowing the measurement to be corrected by calculating a compensation factor at step 620. For example if the measurement is performed at the wrong time of day, a correction factor can be applied based on the subject's expected fluid changes throughout the day.

If the measurement is not usable and not correctable, a notification can be displayed at step 622, for example informing the user of which criteria were not met. At this stage a fluid status indicator can still optionally be displayed at step 624, to provide information to the user, depending on the selected measurement protocol. The process could then perform additional steps similar to those outlined below and these will not therefore be described in further detail.

Alternatively, if it is determined that the measurement is usable or correctable at step 626 the server retrieves a subject normal range from the user data and operates to calculate one or more parameter values at step 628, optionally using the compensation factor as required. As previously discussed, the nature of the parameter values can vary depending on the preferred implementation. In one example, this can include impedance parameter values, but could also include body state indicators derived from the impedance parameter values, such as levels of intra or extracellular fluids.

Figure 8F:
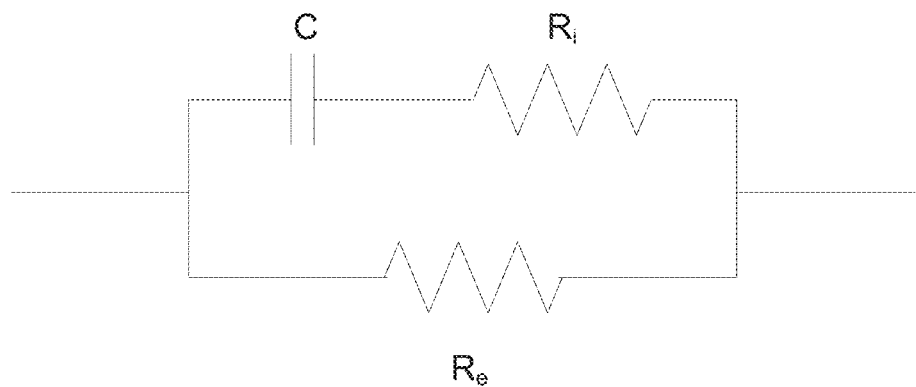
FIG. 8F is schematic diagram of an example of a theoretical equivalent circuit for biological tissue.

In this regard, FIG. 8F is an example of an equivalent circuit that effectively models the electrical behaviour of biological tissue. The equivalent circuit has two branches that represent current flow through extracellular fluid and intracellular fluid, respectively. The extracellular fluid component of biological impedance is represented by an extracellular resistance $R_e$, whilst the intracellular fluid component is represented by an intracellular resistance $R_i$ and a capacitance C representative of the cell membranes.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals the extracellular resistance $R_e$. At infinite frequency the capacitor acts as a perfect conductor and the current passes through the parallel resistive combination. The resistance at infinite frequency $R_\infty$ is given by:

$$R_\infty = \frac{R_e R_i}{R_e + R_i} \quad (1)$$

Hence the intracellular resistance is given by:

$$R_i = \frac{R_\infty R_e}{R_e - R_\infty} \quad (2)$$

Accordingly, the impedance of the equivalent circuit of FIG. 8F at an angular frequency $\omega$, where $\omega=2\pi*$frequency, is given by:

$$Z = R_\infty + \frac{R_0 - R_\infty}{1 + (j\omega\tau)} \quad (3)$$

where: $R_\infty$=impedance at infinite applied frequency
$R_0$=impedance at zero applied frequency=$R_e$ and,
$\tau$ is the time constant of the capacitive circuit.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^\alpha} \quad (4)$$

where: $\alpha$ has a value between 0 and 1 and can be thought of as an indicator of the deviation of a real system from the ideal model.

Figure 8G:
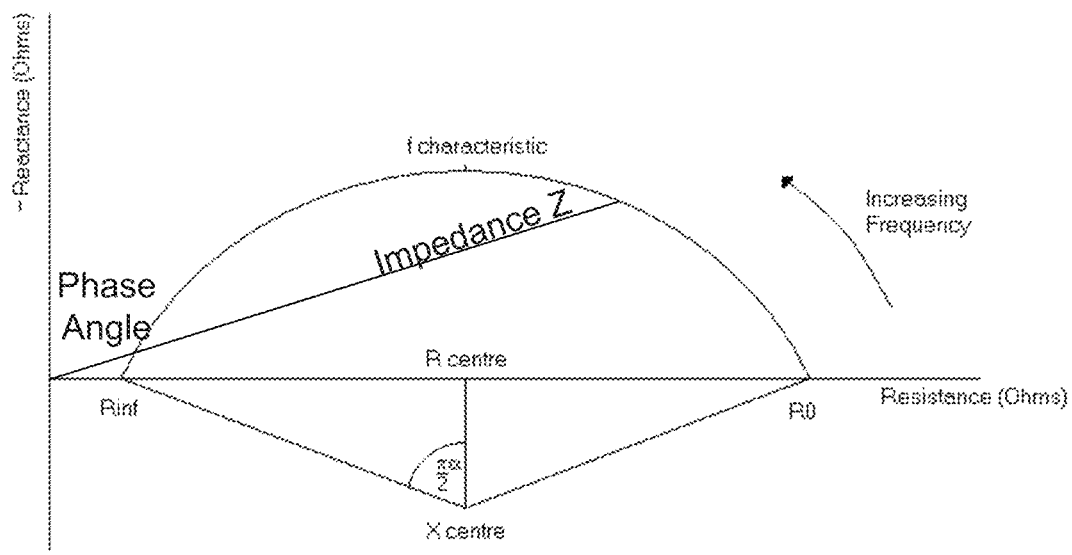
FIG. 8G is an example of a locus of impedance known as a Wessel-plot.

An example of the typical multi-frequency impedance response is shown in FIG. 8G. As frequency increases, the reactance increases to a peak at the characteristic frequency and then decreases while the resistance continually decreases. This results in a circular locus with the centre of the circle below the x axis, as shown.

Whilst the measured impedance can be used directly, in one example, the measured impedance is used to derive an impedance parameter, such as an impedance (resistance) at zero frequency, $R_0$, which equals the extracellular resistance $R_e$, or the impedance at a theoretical infinite frequency $R_\infty$, which can be used with $R_0$ to derive an intracellular resistance $R_i$, as well as other impedance parameters. The values of impedance parameters $X_c$, $R_0$, $R_\infty$, $Z_c$ or $\alpha$ may be determined in any one of a number of manners such as by:
  estimating values based on impedance measurements performed at selected respective frequencies;
  solving simultaneous equations based on the impedance values determined at different frequencies;
  using iterative mathematical techniques;
  extrapolation from a plot of resistance against reactance for impedance measurements at a plurality of frequencies (a "Wessel plot" similar to that shown in FIG. 3B);
  performing a function fitting technique, such as the use of a polynomial function.

For example, the Wessel plot is often used in BIS devices, which perform multiple measurements over a range of frequencies, such as from 1 kHz or 3 kHz to 1000 kHz, using 256 or more different frequencies within this range. A regression procedure is then used to fit the measured data to the theoretical semi-circular locus, allowing values for $X_c$, $R_0$, $R_\infty$, $Z_c$ or $\alpha$ to be calculated. Alternatively, a circle fitting technique can be used in which three simultaneous equations representing the geometric relationships between points on a circle are solved to allow calculation of the radius (r) and the co-ordinates of the centre of the circle (i, j) as the three parameters which define the circle.

In one example, the frequencies used are in the range 0 kHz to 1000 kHz, and in one specific example, four measurements are recorded at frequencies of 25 kHz, 50 kHz, 100 kHz, and 200 kHz, although any suitable measurement frequencies can be used.

A further alternative for determining impedance parameter values such as $X_c$, $R_0$, $R_\infty$, $Z_c$ or $\alpha$ is to perform impedance measurements at a single frequency, and use these as an estimate of the parameter values. In this instance, measurements performed at a single low frequency (typically less than 50 kHz) can be used to estimate $R_0$, measurements at a single high frequency (typically more than 100 kHz) can be used to estimate $R_\infty$, allowing a value of $R_i$ to be determined using equation (2) above.

The above described equivalent circuit models the resistivity as a constant value and does not therefore accurately reflect the impedance response of a subject, and in particular does not accurately model the change in orientation of the erythrocytes in the subject's blood stream, or other relaxation effects. To more successfully model the electrical conductivity of the human body, an improved CPE based model may alternatively be used.

In any event, it will be appreciated that any suitable technique for determination of the parameter values such as $R_0$, $Z_c$, $R_\infty$, and $X_c$ may be used, hence allowing $R_i$ to be derived.

Once the impedance parameter values are determined, additional body state values, such as indications of fluid level values, measures of body composition parameters, or indicators of specific conditions, such heart failure, lymphedema, or the like, can be derived.

The body state values could be indicative of a specific condition, or could be a general indication of a measured body parameter value that is in turn indicative of a condition, such as one or more of Body Composition, Dry Lean Mass, Lean Body Mass, Skeletal Muscle Mass, Segmental Lean Analysis, Body Fat Mass, Segmental Fat Analysis, BMI (Body Mass Index), (Percent Body Fat), Visceral Fat Area, Visceral Fat Level, Total Body Water, Intracellular Water, Extracellular Water, ECW/TBW, Segmental Body Water, Segmental ECW/TBW, Segmental ICW Analysis, Segmental ECW Analysis, Body-Fat-LBM Control, BMR (Basal Metabolic Rate), Leg Lean Mass, TBW/LBM, Whole Body Phase Angle, Segmental Phase Angle, Reactance, Impedance of Each Segment per frequency, or Body Water Composition History. The body state could also be indicative of a general level of athletic fitness, such as whether the individual is fit or unfit.

In a further example, the body parameter value could be based on changes in impedance compared to impedance values associated with a subject normal value, in which case the subject parameter value can be calculated using the equation:

$$PV = B_{PV} + x\Delta I \qquad (5)$$

where: PV is the parameter value
$B_{PV}$ is the subject normal parameter value
x is a coefficient
$\Delta I$ is the difference between the subject normal impedance value and the measured impedance value.

It will be appreciated that the above equation may vary depending on the presence of any correction factor.

At step 630, the calculated parameter value is compared to the subject normal range. If it is determined that the parameter is outside the range at step 632 a count is reset at step 634 otherwise it is incremented at step 636. The count is then compared to a threshold, also typically retrieved from user data, at step 638 to determine if the threshold is exceeded at step 640.

If the threshold has been exceeded, a new normal value and range can be calculated at step 642. The manner in which the new normal value and range is calculated will depend on the preferred implementation, but in one example, this is based on an average of the parameter values that fall outside the previous normal value range, optionally excluding outlier values. The average of the parameter values is used to establish the new subject normal value, with the standard deviation being used to establish the subject normal range, for example basing this on one or two standard deviations from the normal.

An example of this will now be described in more detail with reference to FIGS. 7A to 7C.

Figure 7A:
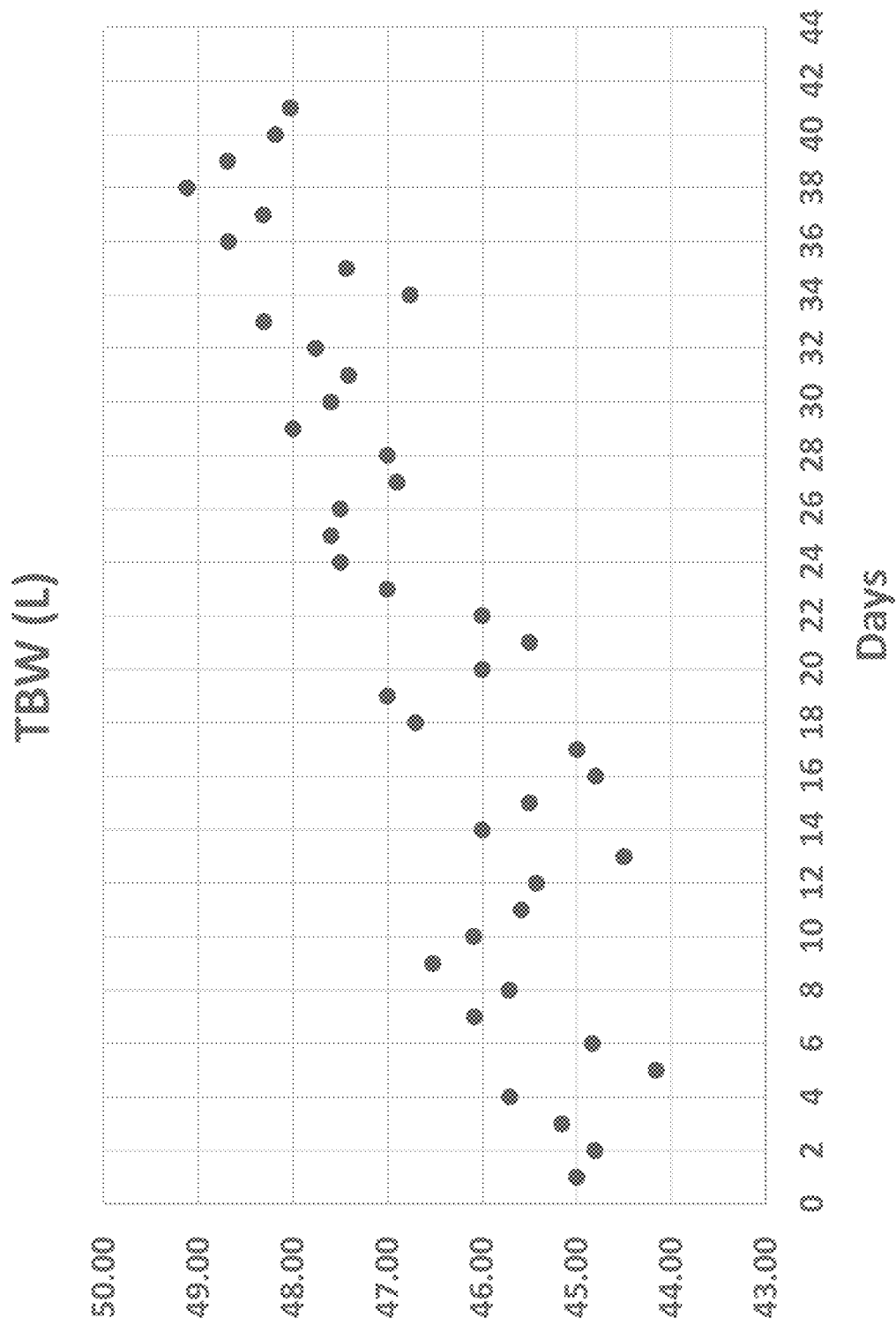
FIG. 7A is a graph showing example total body water measurements.
Figure 7B:
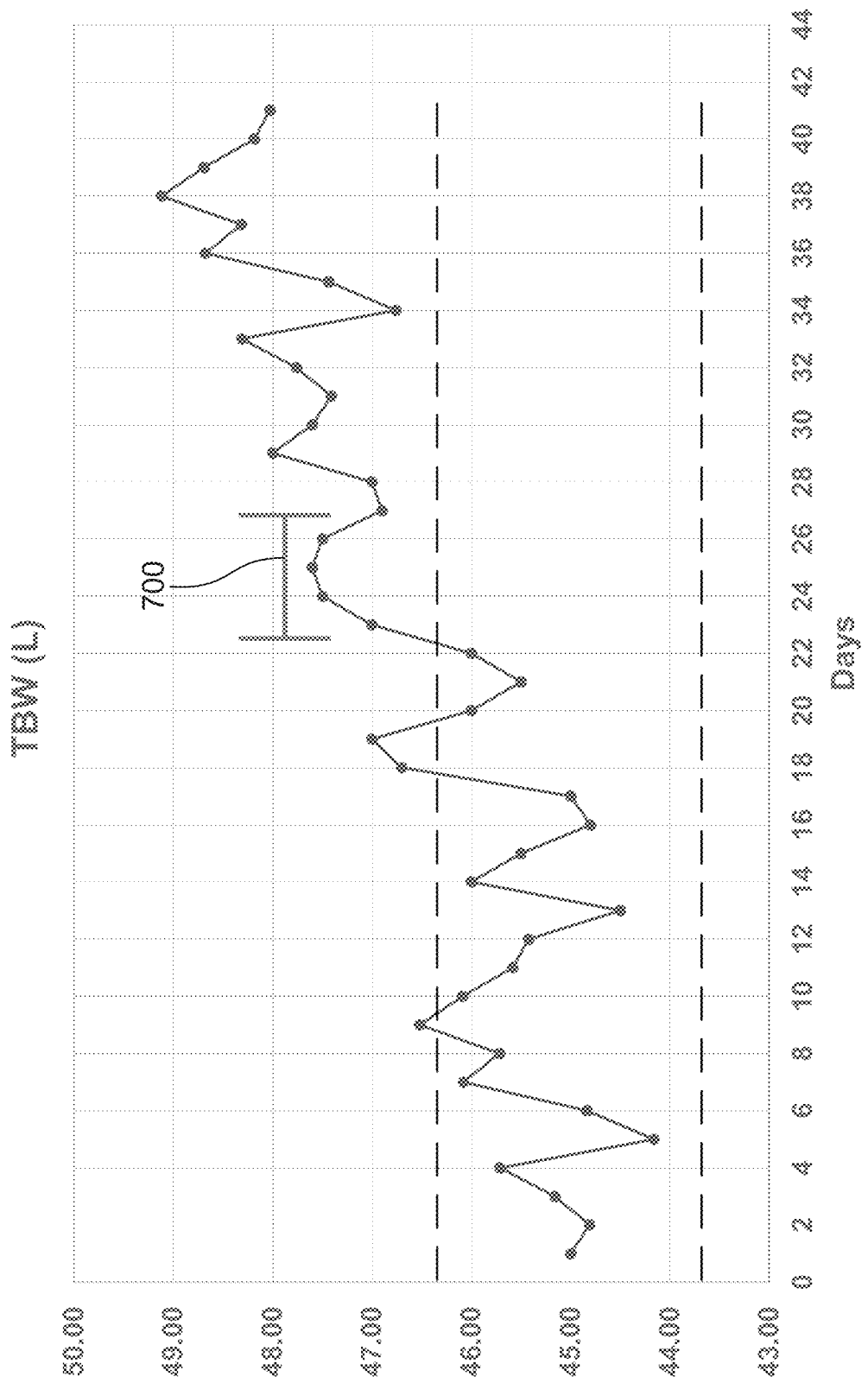
FIG. 7B is a graph showing the total body water measurements of FIG. 7A compared to thresholds.

Specifically, a number of TBW measurements are shown in FIG. 7A, which highlight how calculated TBW values vary significantly between measurements, with day to day variations potentially obscuring a generally upward trend in values. A normal range is shown by the dotted lines in FIG. 7B, with this highlighting that a number of sequential measurements 700 fall outside the normal range, triggering updating of the normal range. Accordingly, at this time a new normal range is calculated based on an average and two standard deviations of the TBW measurements 700. This process is further shown in FIG. 7C, with a first normal range 702 being calculated based on measurements 701, and with a second normal range 704 being calculated based on measurements 703, which fall outside the first normal range 703.

Figure 7C:
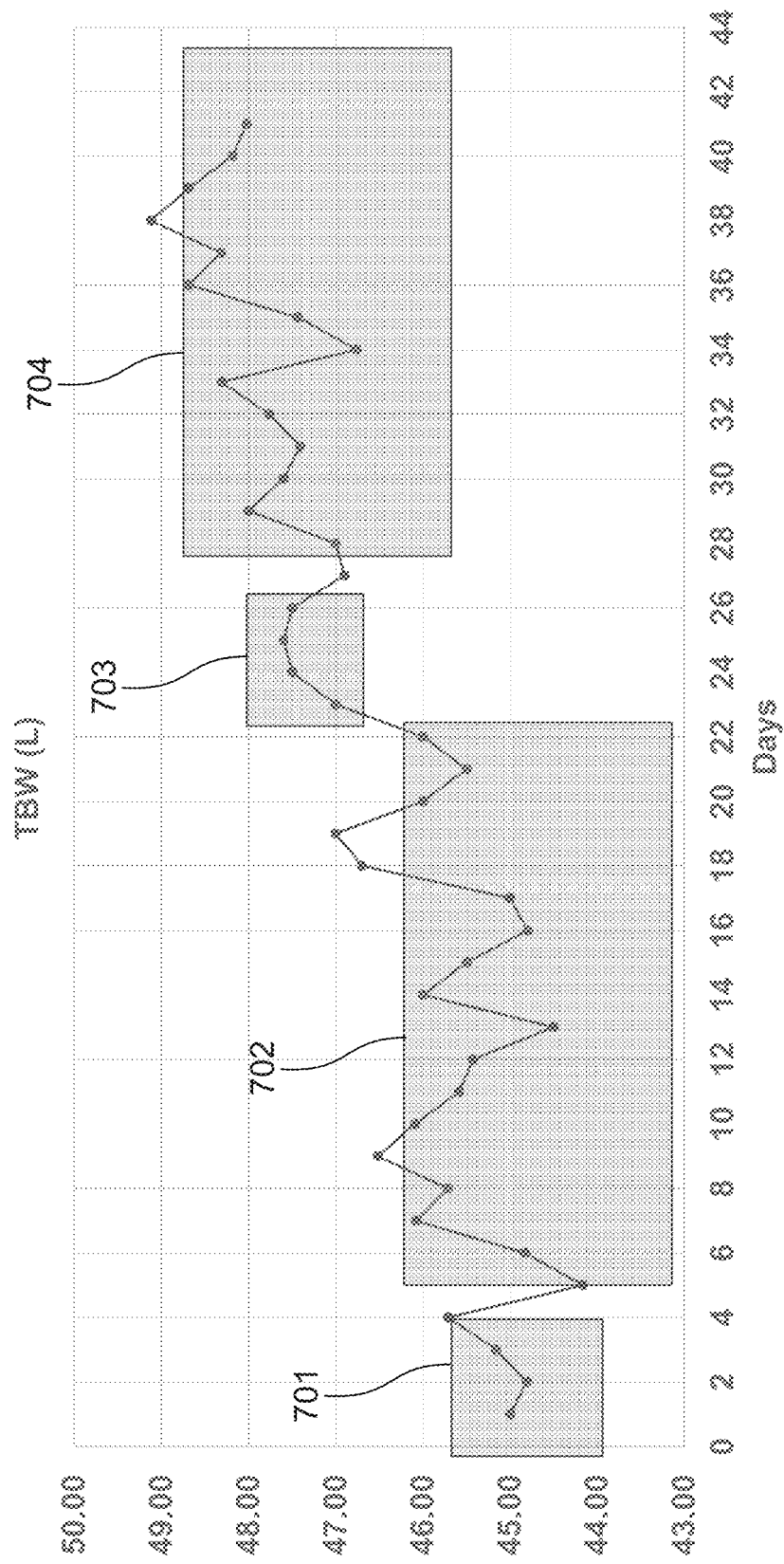
FIG. 7C is a graph showing the calculation of subject normal values and subsequent indicators.

It will be appreciated that in one example, a representation similar to that shown in FIG. 7C can be displayed to a user, or medical practitioner, allowing them to view how changes in measured parameter values and the subsequent impact on the calculated subject normal values and ranges.

Once the new subject normal range has been calculated, a notification can be provided if needed at step 646, for example to alert the user or a medical practitioner with required information.

Following this, or if the threshold is not exceeded, a trend can be stablished based on changes in parameter values at step 646. This could be based on a gradient of a slope established by performing a regression using a number of previous measurements, such as the last 5 or 10 measurements, to determine a general direction and rate of change of the parameter values. The trend can then be compared to a threshold at step 648 and optionally used to predict a future value at step 650, such as a future parameter value, future normal range, the time at which a target will be met, or the like.

At step 652 an indicator can be generated and stored and/or displayed. The indicator can be based on the current subject normal value, but may also be based on trending and/or predictions. For example, the indicator could indicate whether the parameter values are increasing or decreasing relative to the subject normal value, which can be used to inform the user to the fact that there are changes in the parameter value, but that these are not sufficient to be yet considered as meaningful. Similarly a time needed to reach a target, such as a specific goal, can be displayed, for example to encourage the subject to adhere to a treatment regime, behavioural pattern or the like.

Figure 9A:
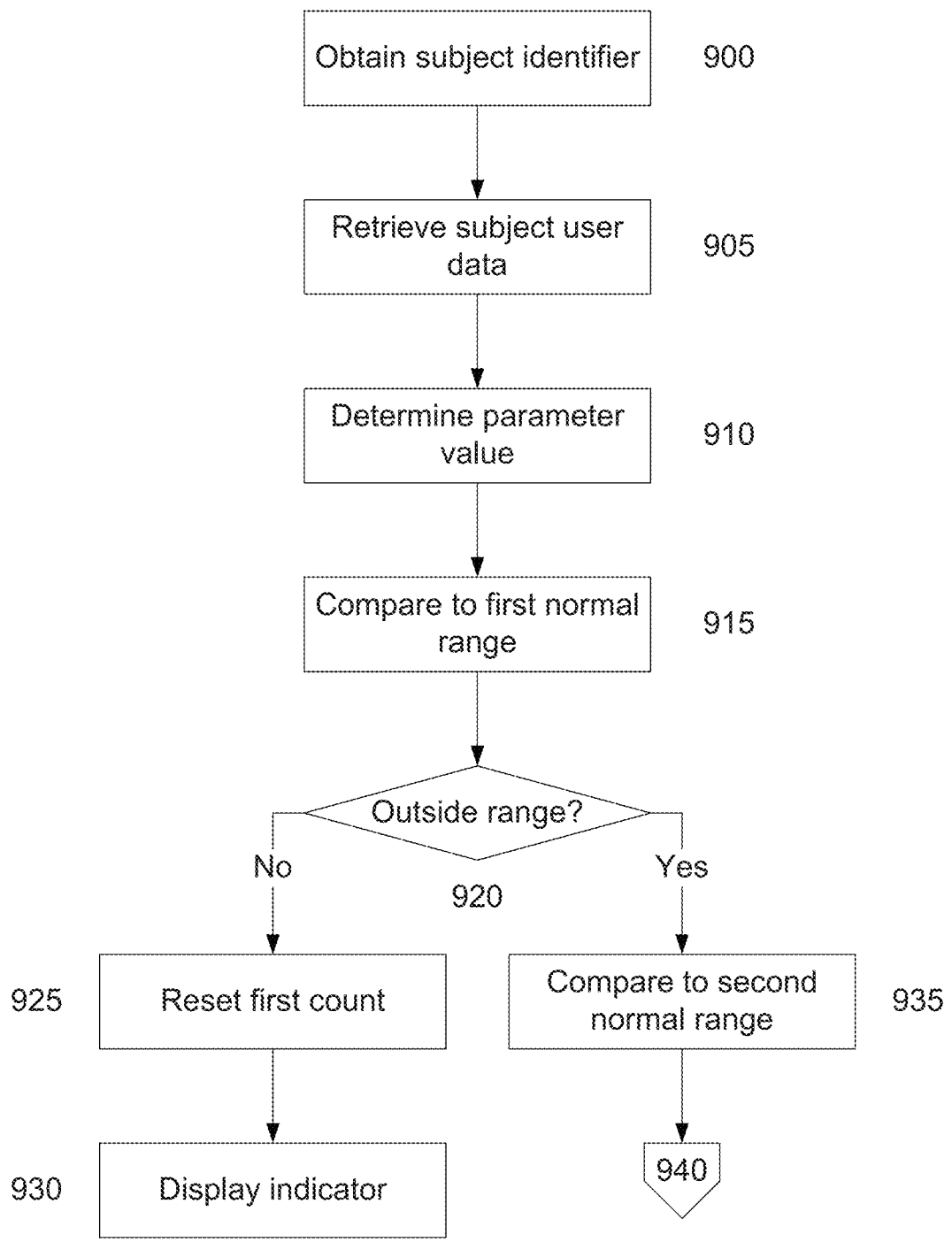
FIGS. 9A and 9B are a flow chart of a further example of a method of processing a parameter value.
Figure 9B:
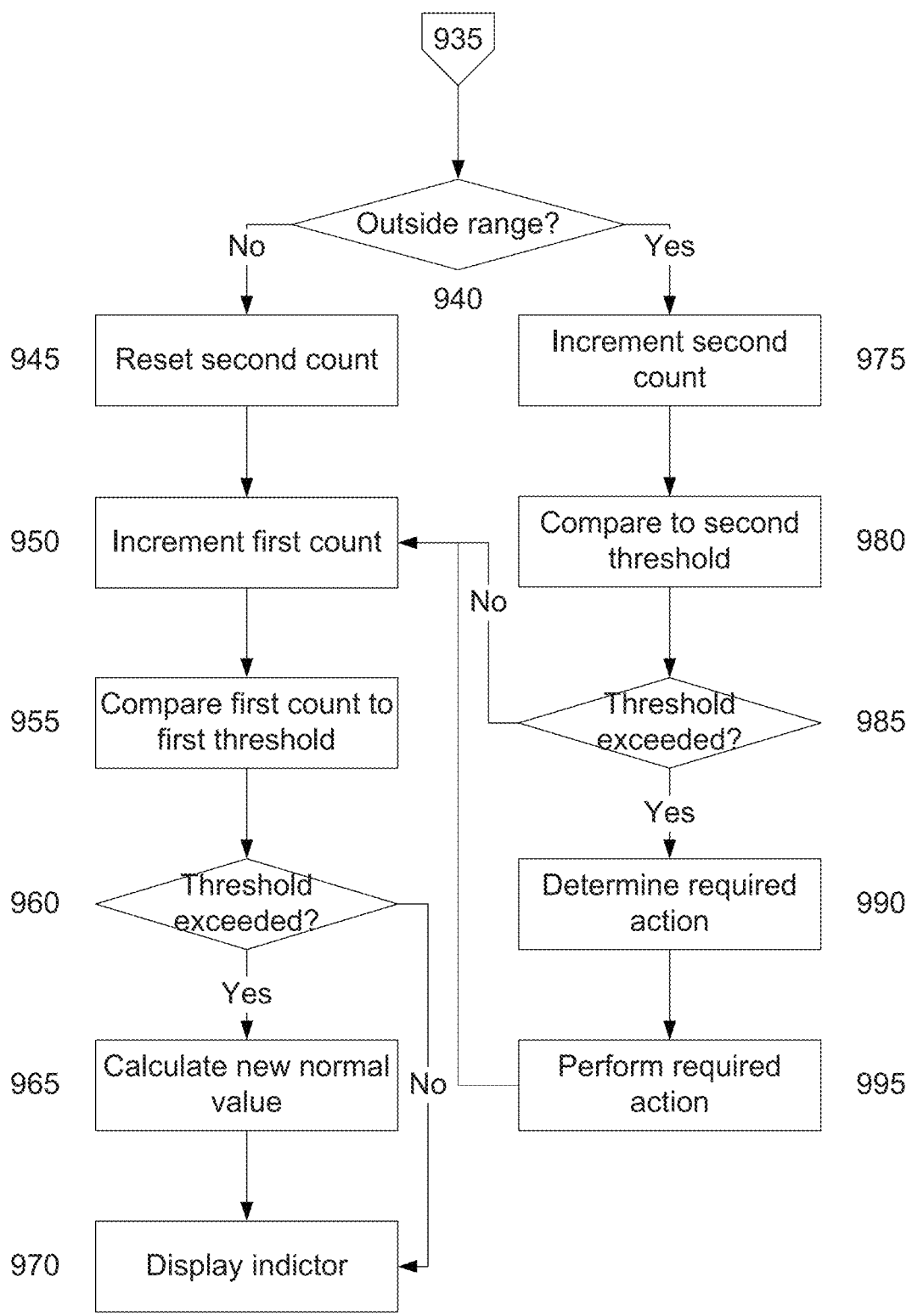

A variation on the above described process to accommodate multiple normal ranges, will now be described with reference to FIGS. 9A and 9B.

In this example, at step 900 a subject identifier is determined from received subject data, with this being used to retrieve subject user data at step 905. A parameter value is then determined from the subject data at step 910, as described for example with respect to step 624 above. The parameter value is compared to a first subject normal range, for example based on two standard deviations, is retrieved from the user data, at step 915 to determine if the parameter value falls out of the first subject normal range at step 920. If not, the first count is reset at step 925 and the process will typically continue as previously described at step 638, allowing an indicator to be optionally displayed at step 930.

Otherwise, at step 935 a second subject normal range, for example based on three standard deviations, is retrieved with the parameter value being compared to the second subject normal range, to determine if the parameter value is outside of the second range at step 940. If it is not outside the second normal range a second count is reset at step 945 before a first count is incremented at step 950. The process then compares the first count to the first threshold at step 955 to determine if the first threshold is exceeded at step 960 and if so a new subject normal value can be calculated at step 965, with an indicator based on the previous or new subject normal then being displayed at step 970, for example as previously described with respect to steps 642 and 644.

Otherwise, if the second parameter value is outside the second range a second count is incremented at step 975 with this being compared to a second threshold at step 980 to determine if the second threshold is exceeded at step 985. If not, the process returns to step 950 to increment the first count otherwise, at step 990 it is determined if an action is required. In this regard, an action would typically be defined as part of the user data, and may specify for example generating a notification and providing this to a medical practitioner, alerting the practitioner to an adverse medical condition. If so this is performed at step 995, before the process returns to step 950 to increment the first count.

Accordingly, the above described arrangements provide a mechanism to allow for the assessment of whether changes in measured parameters are meaningful, using this to tailor the information that is presented to users. In one example, this is achieved by using a dynamic normal range based on previous measurements, assessing whether subsequent measurements fall within or outside the normal range, and displaying indicators to the user based on the result of the assessment. In another example, this is achieved by assessing whether measurements are performed in accordance with defined measurement criteria, only classifying them as meaningful if the criteria are met. It will be appreciated that features from different examples above may be used in conjunction and/or interchangeably where appropriate, so that in a preferred example, changes in measured values are only assessed as meaningful if the measurements meet the defined measurement criteria and the measured values form part of a sequence of measured values falling outside a defined normal range.

The above described approach can be used for a wide range of different parameters, but are particularly suited to measurements of fluid levels, which are often subject to a wide range of variations based on external factors and day to day variations, which are not otherwise necessarily meaningful.

Furthermore, whilst the above examples have focused on a subject such as a human, it will be appreciated that the measuring device and techniques described above can be used with any animal, including but not limited to, primates, livestock, performance animals, such race horses, or the like.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The invention claimed is:

1. A system for generating an indicator at least in part relating to fluid levels in a biological subject, the system including:

a) a measuring system that includes a measuring device that performs at least one impedance measurement on the biological subject and which is indicative of fluid levels in the biological subject, the measurement device including:
  i) at least one signal generator electrically connected to drive electrodes to apply a drive signal to the biological subject;
  ii) at least one sensor electrically connected to sense electrodes to measure a response signal in the biological subject;
  iii) a measuring device processor that at least in part:
    (1) controls the at least one signal generator;
    (2) receives an indication of a measured response signal from the at least one sensor; and,
    (3) generates measurement data indicative of the at least one impedance measurement; and,
b) one or more processing devices that, in response to the at least one impedance measurement:
  i) receive the measurement data;
  ii) determine a parameter value of the at least one impedance measurement using the measurement data;
  iii) perform an assessment to determine if the parameter value is indicative of a meaningful change in a subject normal, the subject normal being a value or range accounting for a spread in the parameter value based on a plurality of previous impedance measurements performed on the biological subject, the parameter value being indicative of a meaningful change where at least one of:
    (1) a measured value of the parameter value is indicative of a change of a condition; and,
    (2) variations in the parameter value are indicative of a change of a condition; and
  iv) use results of the assessment to:
    (1) generate the indicator indicative of fluid levels; and,
    (2) update the subject normal in response to a determination that the parameter value is indicative of a meaningful change,
wherein the measuring system further includes a client device in communication with the measuring device, wherein the client device:
  i) receives the measurement data; and,
  ii) provides subject data to the one or more processing devices via a communications network, the subject data being indicative of at least one of:
    (1) a user identifier associated with the biological subject;
    (2) the measurement data;
    (3) one or more measured impedance values;
    (4) one or more parameter values;
    (5) one or more vital signs indicators; and,
    (6) one or more measurement attributes.

2. The system according to claim 1, wherein the one or more processing devices perform the assessment using a computational model embodying a relationship between the parameter value and the subject normal, the computational model being obtained by applying machine learning to reference parameter values and subject normal measured for one or more reference subjects and wherein the one or more processing devices:

a) determine at least one metric indicative of at least one of
   i) the parameter value including at least one of:
      (1) an impedance value indicative of a measured impedance;
      (2) an impedance parameter value derived from at least one impedance value; and,
      (3) a body state value derived from at least one of:
         (a) at least one impedance value; and,
         (b) at least one impedance parameter value,
   ii) a vital sign indicator indicative of at least one of:
      (1) a cardiac parameter value;
      (2) a respiratory parameter value;
      (3) a blood potassium level;
      (4) a temperature;
      (5) a tissue temperature;
      (6) a blood pressure;
      (7) a respiratory rate;
      (8) a heart rate; and,
      (9) a blood oxygenation level; and,
   iii) a measurement attribute including at least one of:
      (1) an exercise indicator indicative of participation in exercise;
      (2) a time of day;
      (3) a clothing state;
      (4) a consumption of feed or beverage;
      (5) a weight; and,
   iv) details of one or more medical symptoms;
   v) whether the parameter value falls outside a subject normal range, the subject normal range being at least partially based on results of a plurality of previous impedance measurements;
   vi) a number of parameter values falling outside a subject normal range in a defined time period;
   vii) changes in parameter values;
   viii) a trend in parameter values; and,
   ix) a magnitude of changes in parameter values;
b) apply the at least one metric to the computational model; and,
c) wherein the at least one of the vital sign indicator and the measurement attributes are determined from at least one of signals from a physical characteristic sensor and user inputs.

3. The system according to claim 1, wherein the one or more processing devices perform the assessment by:
a) determining if the parameter value falls outside a subject normal range, the subject normal range being at least partially based on results of a plurality of previous impedance measurements performed on the biological subject;
b) updating a count indicative of a number of parameter values that fall outside the subject normal range in accordance with results of the determination, wherein the count is indicative of at least one of:
   i) a number of sequential parameter values that fall outside the subject normal range and wherein the one or more processing devices reset the count if the parameter value falls inside the subject normal range; and,
   ii) how many of a defined number of impedance measurements fall outside the subject normal range;
c) determining if the count exceeds a threshold; and,
d) based on whether the count exceeds the threshold:
   i) determining if the parameter value is indicative of a meaningful change in a subject normal;
   ii) generating the indicator; and,
   iii) updating the subject normal range in response to a determination that the parameter value is indicative of a meaningful change.

4. The system according to claim 1, wherein at least one of:
a) the indicator is indicative of at least one of:
   i) the parameter value;
   ii) a subject normal value;
   iii) a subject normal range;
   iv) a subject normal parameter value derived from a subject normal value;
   v) whether the parameter value is greater than or lesser than a subject normal value;
   vi) whether the parameter value is greater than or lesser than a subject normal parameter value;
   vii) whether the parameter value falls outside the subject normal range;
   viii) whether the parameter value is greater than or lesser than the subject normal range;
   ix) a magnitude of a difference between the parameter value and a subject normal value;
   x) a magnitude of a difference between the parameter value and a subject normal parameter value;
   xi) a parameter value change;
   xii) a parameter value rate of change; and,
   xiii) a parameter value trend;
b) if the parameter value is not indicative of a meaningful change in a subject normal, the indicator is indicative of at least one of:
   i) a subject normal value;
   ii) that there is no meaningful change from the subject normal value; and,
   iii) a trend indicative of a direction of change of the parameter value relative to the subject normal value; and
c) if the parameter value is indicative of a meaningful change in a subject normal, the indicator is indicative of at least one of:
   i) the parameter value; and,
   ii) an updated subject normal value.

5. The system according to claim 1, wherein the parameter value is at least one of:
a) an impedance value indicative of a measured impedance;
b) an impedance parameter value derived from at least one impedance value; and,
c) a body state value derived from at least one of:
   i) at least one impedance value; and,
   ii) at least one impedance parameter value.

6. The system according to claim 1, wherein the one or more processing devices perform the assessment using a subject normal range based on a subject normal value and wherein the subject normal range includes at least one of:
a) a subject normal fluid level range;
b) a subject normal impedance value range;
c) a subject normal parameter value range; and,
d) a subject normal body state value range.

7. The system according to claim 1, wherein the one or more processing devices:
a) determine a plurality of parameter values, the plurality of parameter values being selected ones of multiple parameter values derived from multiple impedance measurements performed on the biological subject; and, b) calculate, using the plurality of parameter values, at least one of:
i) a subject normal value;
ii) a subject normal range; and,
iii) a body state value.

8. The system according to claim 1, wherein the one or more processing devices calculate at least one of:
a) a subject normal value using at least one of:
i) an average of a plurality of impedance parameter values,
ii) an average of a plurality of parameter values; and,
iii) an average of a plurality of body state values;
b) the subject normal range using at least one of:
i) a spread of at least one of:
(1) a plurality of impedance measurements;
(2) a plurality of parameter values; and,
(3) a plurality of body state values; and,
ii) a predetermined range from a subject normal value; and,
c) the subject normal range taking into account at least one of:
i) details of one or more medical symptoms;
ii) one or more vital signs parameter values; and,
iii) one or more subject attributes.

9. The system according to claim 1, wherein the one or more processing devices:
a) assess if the parameter value falls outside a first subject normal range;
b) selectively update a first count indicative of a number of parameter values falling outside of the first subject normal range;
c) determine if the first count exceeds a first threshold;
d) displays the indicator based on a result of the determination;
e) assess if the parameter value falls outside a second subject normal range;
f) selectively update a second count indicative of a number of parameter values falling outside of the second subject normal range;
g) determine if the second count exceeds a second threshold; and,
h) selectively performs an action based on a result of the determination, wherein the action includes at least one of:
i) updating the subject normal range;
ii) updating the subject normal value; and,
iii) generating a notification.

10. The system according to claim 1, wherein the one or more processing devices calculate, using impedance measurements meeting defined measurement criteria, at least one of:
a) the parameter value;
b) a subject normal value; and,
c) a subject normal range.

11. The system according to claim 1, wherein the one or more processing devices:
a) determine measurement attributes, wherein the measurement attributes include at least one of:
i) an exercise indicator indicative of participation in exercise;
ii) a time of day;
iii) a clothing state;
iv) a consumption of feed or beverage;
v) a weight;
vi) a vital sign indicator; and, b) details of one or more medical symptoms; and
c) compare the measurement attributes to defined measurement criteria to determine if an impedance measurement should be used in calculating at least one of:
i) a parameter value;
ii) a subject normal value;
iii) a subject normal range; and,
d) wherein the at least one of the vital sign indicator and the measurement attributes are determined from at least one of signals a physical characteristic sensor and user inputs.

12. The system according to claim 1, wherein the one or more processing devices:
a) determine at least one parameter value change using multiple parameter values; and,
b) selectively use the parameter value change to determine a parameter value trend indicative of at least one of:
i) a direction of parameter value change;
ii) a rate of parameter value change; and,
iii) a magnitude of parameter value change; and,
c) wherein the one or more processing devices use the parameter value trend to predict at least one of:
i) a future parameter value;
ii) a future subject normal value;
iii) a future subject normal range; and,
iv) a time needed to reach a target.

13. A method for generating in one or more processing devices an indicator at least in part relating to fluid levels in a biological subject using measurement data indicative of at least one impedance measurement performed on the biological subject by a measuring system including a measuring device and a client device in communication with the measuring device, the client device configured to:
i) receive the measurement data; and
ii) provide subject data to the one or more processing devices via a communications network, the subject data being indicative of at least one of:
(1) a user identifier associated with the biological subject;
(2) the measurement data;
(3) one or more measured impedance values;
(4) one or more parameter values;
(5) one or more vital signs indicators; and,
(6) one or more measurement attributes,
the method including in the one or more processing devices, in response to the at least one impedance measurement:
a) receiving the measurement data
b) determining a parameter value of the at least one impedance measurement of the at least one impedance measurement using the measurement data;
c) performing an assessment to determine if the parameter value is indicative of a meaningful change in a subject normal, the subject normal being a value or range accounting for a spread in the parameter value based on a plurality of previous impedance measurements performed on the biological subject, the parameter value being indicative of a meaningful change where at least one of:
i) a measured value of the parameter value is indicative of a change of a condition; and,
ii) variations in the parameter value are indicative of a change of a condition;

d) using results of the assessment to:
  i) generate the indicator indicative of fluid levels; and,
  ii) update the subject normal in response to a determination that the parameter value is indicative of a meaningful change; and,
e) generating a representation of the indication indicative of fluid levels for a display.

14. A system for determining an indicator at least in part relating to fluid levels in a biological subject, the system including:
  a) a measuring system that includes a measuring device that performs at least one impedance measurement on the biological subject, the measurement device including:
    i) at least one signal generator electrically connected to drive electrodes to apply a drive signal to the biological subject;
    ii) at least one sensor electrically connected to sense electrodes to measure a response signal in the biological subject;
    iii) a measuring device processor that at least in part:
      (1) controls the at least one signal generator;
      (2) receives an indication of a measured response signal from the at least one sensor; and,
      (3) generates measurement data indicative of the at least one impedance measurement; and,
  b) a display; and,
  c) one or more processing devices that, in response to the at least one impedance measurement:
    i) receive the measurement data;
    ii) determine a parameter value at least in part using results of the at least one impedance measurement based on the measurement data;
    iii) determine measurement attributes associated with at the least one impedance measurement;
    iv) compare the measurement attributes to defined measurement criteria;
    v) if the measurement criteria meet the defined criteria:
      (1) determine if the parameter value falls outside a subject normal range, the subject normal range being at least partially based on results of a plurality of previous impedance measurements performed on the biological subject;
      (2) based on the result of the determination:
        (a) generate and display the indicator on the display; and,
        (b) update the subject normal range in response to a determination that the parameter value is indicative of a meaningful change; and,
    v) if the measurement criteria do not meet the defined criteria, at least one of:
      (1) display an indicator based on the parameter value on the display; and,
      (2) determine a compensation factor in accordance with results of the comparison, the compensation factor being used to selectively modify at least one of:
        (a) an impedance value indicative of a measured impedance;
        (b) an impedance parameter value derived from at least one impedance value; and,
        (c) a body state value derived from at least one of:
          (i) at least one impedance value; and,
          (ii) at least one impedance parameter value,
wherein the measuring system further includes a client device in communication with the measuring device, wherein the client device:
  i) receives the measurement data; and,
  ii) provides subject data to the one or more processing devices via a communications network, the subject data being indicative of at least one of:
    (1) a user identifier associated with the biological subject;
    (2) the measurement data;
    (3) one or more measured impedance values;
    (4) one or more parameter values;
    (5) one or more vital signs indicators; and,
    (6) one or more measurement attributes.

15. A system for generating an indicator at least in part relating to fluid levels in a biological subject, the system including:
  a) a measuring system that includes a measuring device that performs at least one impedance measurement on the biological subject and which is indicative of fluid levels in the biological subject, the measurement device including:
    i) at least one signal generator electrically connected to drive electrodes to apply a drive signal to the biological subject;
    ii) at least one sensor electrically connected to sense electrodes to measure a response signal in the biological subject;
    iii) a measuring device processor that at least in part:
      (1) controls the at least one signal generator;
      (2) receives an indication of a measured response signal from the at least one sensor; and,
      (3) generates measurement data indicative of the at least one impedance measurement; and,
  b) one or more processing devices that, in response to the at least one impedance measurement:
    i) receive the measurement data;
    ii) determine a parameter value of the at least one impedance measurement using the measurement data;
    iii) perform an assessment to determine if the parameter value falls outside a subject normal range, the subject normal range accounting for a spread in the parameter value based on a plurality of previous impedance measurements performed on the biological subject;
    iv) update a count indicative of a number of parameter values that fall outside the subject normal range in accordance with results of the determination, wherein the count is indicative of at least one of:
      (1) a number of sequential parameter values that fall outside the subject normal range and wherein the one or more processing devices reset the count if the parameter value falls inside the subject normal range; and,
      (2) how many of a defined number of impedance measurements fall outside the subject normal range;
    v) determine if the count exceeds a threshold;
    vi) based on whether the count exceeds the threshold, determine if the parameter value is indicative of a meaningful change; and
    iv) use results of the assessment to:
      (1) generate the indicator indicative of fluid levels; and,
      (2) update the subject normal range in response to a determination that the parameter value is indicative of a meaningful change.

* * * * *